(12) United States Patent
Bullington et al.

(10) Patent No.: US 6,291,454 B1
(45) Date of Patent: Sep. 18, 2001

(54) DITHIEPINO[6,5-B]PYRIDINES, AND RELATED COMPOSITIONS AND METHODS

(75) Inventors: James L. Bullington, Hamilton Square; John H. Dodd, Pittstown; Daniel A. Hall, Somerset, all of NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/580,882

(22) Filed: May 30, 2000

Related U.S. Application Data

(60) Provisional application No. 60/138,987, filed on Jun. 14, 1999.

(51) Int. Cl.$^7$ .......... A61K 31/54; A61K 31/50; A61K 31/44; C07D 471/02; C07D 417/00
(52) U.S. Cl. .......... 514/227.8; 514/252.13; 514/301; 514/231.5; 546/114; 544/61; 544/127; 544/362
(58) Field of Search .......... 546/290, 114; 514/345, 227.8, 252.13, 301, 231.5; 544/61, 127, 362

(56) References Cited

U.S. PATENT DOCUMENTS

| | | | |
|---|---|---|---|
| 4,285,955 | 8/1981 | Wehinger et al. | 424/266 |
| 4,483,985 | 11/1984 | Wehinger et al. | 544/131 |
| 4,532,248 | 7/1985 | Franckowiak et al. | 514/302 |
| 4,845,225 | 7/1989 | Schwender et al. | 546/114 |
| 4,879,384 | 11/1989 | Schwender et al. | 546/114 |
| 4,889,866 | 12/1989 | Pfister et al. | 514/347 |
| 4,918,087 * | 4/1990 | Gandolfi et al. . | |
| 5,075,440 | 12/1991 | Wustrow et al. | 540/468 |
| 5,708,177 | 1/1998 | Straub | 546/257 |

FOREIGN PATENT DOCUMENTS

| | | |
|---|---|---|
| 462696 | 12/1991 | (EP) . |
| 2 178 738 | 6/1986 | (GB) . |
| 58201764 | 11/1983 | (JP) . |

OTHER PUBLICATIONS

Dodd et al., Drug Des. Discov. 1997 15:135–48.
Dodd et al., Drug Des. Discov. 1993, 10:65–75.
Pagani, G.P.A., J. Chem. Soc. Perkin Trans. 2, 1392 (1974).
Biggadike et al., 2000, J. Med. Chem. 43:19–21.
Lee et al., 1998, Curr. Opin. Drug Disc. Dev. 1: 235–44.
Edema et al., J. Org. Chem. 58: 5624–7, 1993.
Howard et al., J. Amer. Chem. Soc. 82:158–64, 1960).
Eistert et al. (Chem. Ber. 110, 1069–1085, 1977).
Mason et al. (J. Chem. Soc. (C) 2171–76, 1967.)
E. A. Fehnel (J. Amer. Chem. Soc. 74, 1569–74, 1952).

\* cited by examiner

*Primary Examiner*—Alan L. Rotman
*Assistant Examiner*—Binta Robinson
(74) *Attorney, Agent, or Firm*—Kenneth J. Dow

(57) ABSTRACT

This invention provides novel dithiepino[6,5-b]pyridines of the following formulae.

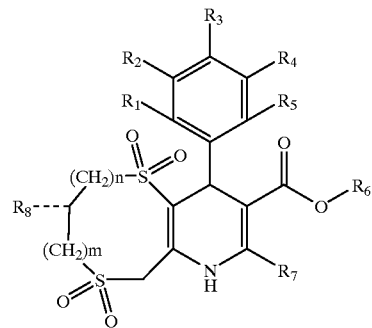

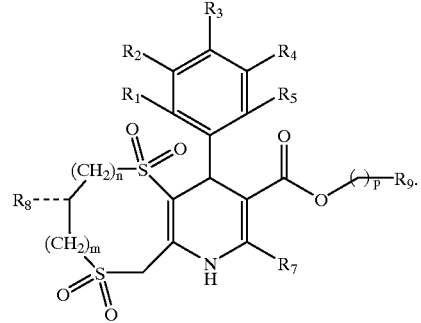

These compounds are useful as calcium channel antagonists with cardiovascular, antiasthinatic and antibronchoconstriction activity. Thus, this invention also provides pharmaceutical compositions, as well as methods, for preventing and treating disorders such as hypersensitivity, allergy, asthma, bronchospasm, dysmenorrhea, esophageal spasm, glaucoma, premature labor, urinary tract disorders, gastrointestinal motility disorders and cardiovascular disorders.

58 Claims, No Drawings

DITHIEPINO[6,5-B]PYRIDINES, AND RELATED COMPOSITIONS AND METHODS

This application claims benefit of Ser. No. 60/138,987 expired filed Jun. 14, 1999.

FIELD OF THE INVENTION

This invention relates to novel dithiepino[6,5-b]pyridines useful as calcium channel blockers. These compounds, and related pharmaceutical compositions, are useful for treating and preventing a number of disorders such as hypersensitivity, allergy, asthma, bronchospasm, dysmenorrhea, esophageal spasm, glaucoma, premature labor, urinary tract disorders, gastrointestinal motility disorders and cardiovascular disorders.

BACKGROUND OF THE INVENTION

Thiacycloalkeno[3,2-b]pyridines are inhibitors of calcium ion uptake into smooth muscle tissue. They act to relax or prevent contraction of tissue mediated by calcium mechanisms (Dodd et al., Drug Des. Discov. 1997 15:135–48). These compounds are active antihypertensives and bronchodilators.

Thiacycloalkeno[3,2-b]pyridines are also useful for the treatment of cardiovascular disorders, including hypertension, ischemia, angina, congestive heart failure, migraines, myocardial infarction and stroke. Such compounds are also useful for the treatment of other disorders such as hypersensitivity, allergy, asthma, dysmenorrhea, esophageal spasm, gastrointestinal motility disorders, glaucoma, premature labor and urinary tract disorders.

Dodd et al. evaluated a series of thiacycloalkeno[3,2-b] pyridines ranging in sulfone ring size from five to nine members for calcium antagonist activity. It was found that increasing the sulfone ring size from 5 to 8 members results in an in vitro potency increase of two orders of magnitude. Aromatic substitution patterns which favor tracheal effects over aortic effects were found to be 2—$NO_2$ and 2—Cl, 6—F. The ester side chain which was found to maximize in vivo activity was the N-benzyl-N-methyl aminoethyl moiety (Dodd et al., Drug Des. Discov. 1997, 15:135–48, and Drug Des. Discov. 1993, 10:65–75).

Numerous compounds related to thiacycloalkeno[3,2-b] pyridines are known, as exemplified by the following publications. U.S. Pat. No. 5,708,177 to Straub discloses a process for the preparation of optically active ortho-substituted 4-aryl- or heteroaryl-1,4-dihydropyridines by oxidation and subsequent reduction from their opposite enantiomers. U.S. Pat. No. 5,075,440 to Wustrow et al. discloses pyrido[2,3-f] [1,4]thiazepines and pyrido[3,2-b] [1,5]benzothiazepines which are useful as calcium channel antagonists with cardiovascular, antiasthmatic and antibronchoconstriction activity. U.S. Pat. Nos. 4,879,384 and 4,845,225, both to Schwender and Dodd, disclose substituted thiacycloalkeno [3,2-b] pyridines which are also useful as calcium channel antagonists with cardiovascular, antiasthmatic and antibronchoconstrictor activity. U.S. Pat. Nos. 4,285,955 and 4,483,985 disclose acyclic sulfone (substitution on simple dihydropyridines which possess calcium channel antagonist activity. U.S. Pat. No. 4,532,248 discloses a broad genus of dihydropyridines, including cyclic sulfones fused to a dihydropyridine nucleus. Cardiotonic activity is disclosed for the entire genus. Finally, 10-Phenyl-2H-thiopyranol[3,2-b]quinolines are disclosed in Pagani, G.P.A., J. Chem. Soc. Perkin Trans. 2, 1392 (1974). However, these compounds are not calcium channel antagonists. "Soft drugs" (also known as "antedrugs") are biologically active drugs which are metabolically inactivated after they achieve their therapeutic role at their designed site of action. The use of soft drugs, instead of their non-inactivatable analogs, avoids unwanted side effects. Soft drugs are known generally (see, for example, Biggadike et al., 2000, J. Med. Chem. 43:19–21; Lee et al., 1998, Curr. Opin. Drug Disc. Dev. 1: 235–44). However, no dihydropyridine soft drugs are known.

SUMMARY OF THE INVENTION

This invention provides novel dithiepino[6,5-b]pyridines as defined hereinbelow, as well as methods for making same. This invention also provides a pharmaceutical composition comprising the instant compound and a pharmaceutically acceptable carrier.

This invention further provides a method of treating a subject suffering from a disorder whose alleviation is mediated by the reduction of calcium ion influx into cells whose actions contribute to the disorder, which method comprises administering to the subject a therapeutically effective dose of the instant pharmaceutical composition.

This invention slill further provides a method of inhibiting in a subject the onset of a disorder whose alleviation is mediated by the reduction of calcium ion influx into cells whose actions contribute to the disorder, which method comprises administering to the subject a prophylactically effective dose of the instant pharmaceutical composition.

Finally, this invention provides an apparatus for administering to a subject the instant pharmaceutical composition, comprising a container and the pharmaceutical composition therein, whereby the container has a means for delivering to the subject a therapeutic and/or prophylactic dose of the pharmaceutical composition.

DETAILED DESCRIPTION OF THE INVENTION

This invention provides a compound of Formula I,

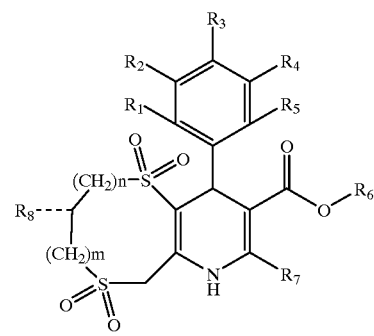

Formula I or a pharmaceutically a:cceptable salt thereof, wherein
(a) $R_1$, $R_2$, $R_3$, $R_4$ and $R_5$ are independently selected from the group consisting of H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl, and oxadiazole (formed by $R_1$ and $R_2$);
(b) $R_6$ is selected from the group consisting of H, $C_{1-5}$ straight or branched alkyl, aryl, 3-piperidyl, N-substituted 3-piperidyl, N-substituted 2-pyrrolidinyl methylene, and substituted alkyl, wherein said N-substituted 3-piperidyl and said N-substituted 2-pyrrolidinyl methylene may be substituted with $C_{1-8}$ straight or branched chain alkyl or benzyl, and said substituted alkyl may be substituted with $C_{1-8}$ alkoxy, $C_{2-8}$ alkanoyloxy, phenylacetyloxy, benzoyloxy, hydroxy, halogen, p-tosyloxy, mesyloxy, amino, carboalkoxy or NR'R", wherein
  (i) R' and R" are independently selected from the group consisting of H, $C_{1-8}$ straight or branched alkyl, $C_{3-7}$ cycloalkyl, phenyl, benzyl, and phenethyl, or (ii) R' and R" together form a heterocyclic ring selected from the group consisting of piperidino, pyrrolidino, morpholino, thiomorpholino, piperazino, 2-thieno, 3-thieno, and an N-substituted derivative of said heterocyclic rings, said N-substituted derivative being substituted with H, $C_{1-8}$ straight or branched alkyl, benzyl, benzhydryl, phenyl and/or substituted phenyl (substituted with $NO_2$, halogen, $C_{1-8}$ straight or branched chain alkyl, $C_{1-8}$ alkoxy and/or trifluoromethyl);

(c) $R_7$ is selected from the group consisting of H, amino, alkyl, aryl, trifluoromethyl, alkoxymethyl, 2-thieno and 3-thieno;

(d) $R_8$ is connected to the bis-sulfone ring via a single or double bond, as applicable, and is selected from the group consisting of H, alkylhydroxy, alkenyl, amino, phenyl, benzyl, $C_{1-8}$ straight or branched alkyl, trifluoromethyl, alkoxymethyl, $C_{3-7}$ cycloalkyl, substituted benzyl, formyl, acetyl, t-butyloxy carbonyl, propionyl, substituted alkyl and R'''$CH_2$C=O, wherein (i) said substituted benzyl is substituted with halogen, trifluoromethyl, $C_{1-8}$, straight and/or branched alkyl or $C_{1-8}$ alkoxy, (ii) said substituted alkyl is substituted with amino, dialkyl amino, $C_{1-8}$ alkoxy, hydroxy and/or halogen, and (iii) R''' is amino, dialkyl amino, $C_{1-8}$, alkoxy, hydroxy or halogen; and (e) m, n, and their sum are each an integer from 0 to 4.

In one embodirrent of the instant compound, $R_6$ is —$(CH_2)_2N(CH_3)CH_2PH$. In another embodiment, $R_6$ is methyl, and preferably, (a) $R_4$ is $CF_3$, $R_5$ is F, $R_7$ is methyl, $R_8$ is methylene, m is 0 and n is 1, or (b) $R_4$ is $CF_3$, $R_5$ is F, $R_7$ is methyl, $R_8$ is alkylhydroxy, m is 0 and n is 1. In a further embodiment, $R_7$ is methyl, and preferably (a) $R_6$ is —$(CH_2)_2N(CH_3)CH_2PH$, (b) $R_4$ is $CF_3$ and $R_5$ is F, (c) $R_5$ is Cl, or (d) $R_1$ is F and $R_5$ is Cl.

The following compounds are preferred embodiments of the present invention.

5H-1,4-Dithiepino[6,5-b]pyridine-8-carboxylic acid, 9-(2-chloro-6-fluorophenyl)-2,3,6,9-tetrahydro-7-methyl-2-[methyl(phenylmethyl)amino]ethyl ester 1,1,4,4-tetraoxide;

5H-1,4-Dithiepino[6,5-b]pyridine-8-carboxylic acid, 2,3,6,9-tetrahydro-7-methyl-9-(3,4,5-trifluorophenyl)-2-[methyl(2-thienylmethyl)amino]ethyl ester 1,1,4,4-tetraoxide;

5H-1,4-Dithiepino[6,5-b]pyridine-8-carboxylic acid, 9-[2-fluoro-6-(trifluoromethyl)phenyl]-2,3,6,9-tetrahydro-7-methyl-2-[methyl(phenylmethyl)amino] ethyl ester 1,1,4,4-tetraoxide;

5H-1,4-Dithiepino[6,5-b]pyridine-8-carboxylic acid, 9-(2-chloro-6-fluorophenyl)-2,3,6,9-tetrahydro-7-methyl-2-[methyl(phenylmethyl)amino]ethyl ester 1,1,4,4-tetraoxide, (9R);

5H-1,4-Dithiepino[6,5-b]pyridine-8-carboxylic acid, 9-(2-chloro-6-fluorophenyl)-2,3,6,9-tetrahydro-7-methyl-2-[methyl(phenylmethyl)amino]ethyl ester 1,1,4,4-tetraoxide, (9S);

5H-1,4-Dithiepino[6,5-b]pyridine-8-carboxylic acid, 9-(2-chloro-6-hydroxyphenyl)-2,3,6,9-tetrahydro-7-methyl-2-[methyl(phenylmethyl)amino]ethyl ester 1,1,4,4-tetraioxide;

5H-1,4-Dithiepino[6,5-b]pyridine-8-carboxylic acid, 9-(2-chlorophenyl)-2,3,6,9-tetrahydro-7-methyl-2-[methyl(phenylmethyl)amino]ethyl ester 1,1,4,4-tetraoxide;

5H-1,4-Dithiepino[6,5-b]pyridine-8-carboxylic acid, 9-[2-fluoro-3-(trifluoromethyl)phenyl]-2,3,6,9-tetrahydro-7-methyl-2-[methyl(phenylmethyl)amino] ethyl ester 1,1,4,4-tetraoxide;

5H-1,4-Dithiepiro[6,5-b]pyridine-8-carboxylic acid, 2,3,6,9-tetrahydro-7-methyl-9-(3-nitrophenyl)-2-[methyl (phenylmethyl)amino]ethyl ester 1,1,4,4-tetraoxide;

5H-1,4-Dithiepirio[6,5-b]pyridine-8-carboxylic acid, 2,3,6,9-tetrahydro-7-methyl-9-(3,4,5-trifluorophenyl)-2-[methyl(phenylmethyl)amino]ethyl ester 1,1,4,4-tetraoxide;

5H-1,4-Dithiepino[6,5-b]pyridine-8-carboxylic acid, 9-(2-chloro-6-fluorophenyl)-2,3,6,9-tetrahydro-7-methyl-methyl ester 1,1,4,4-tetraoxide;

5H-1,4-Dithiepino[6,5-b]pyridine-8-carboxylic acid, 9-(2-chloro-5-nitrophenyl)-2,3,6,9-tetrahydro-7-methyl-methyl ester 1,1,4,4-tetraoxide;

5H-1,4-Dithiepino[6,5-b]pyridine-8-carboxylic acid, 2,3,6,9-tetrahydro-7-methyl-9-(pentafluorophenyl)-methyl ester 1,1,4,4-tetraoxide;

5H-1,4-Dithiepino[6,5-b]pyridine-8-carboxylic acid, 9-(2,6-difluorophenyl)-2,3,6,9-tetrahydro-7-methyl-methyl ester 1,1,4,4-tetraoxide;

5H-1,4-Dithiepino[6,5-b]pyridine-8-carboxylic acid, 9-(2-chlorophenyl)-2,3,6,9-tetrahydro-7-methyl-methyl ester 1,1,4,4-tetraoxide;

5H-1,4-Dithiepino[6,5-b]pyridine-8-carboxylic acid, 9-(2-fluorophenyl)-2,3,6,9-tetrahydro-7-methyl-methyl ester 1,1,4,4-tetraoxide;

5H-1,4-Dithiepino[6,5-b]pyridine-8-carboxylic acid, 9-[2-fluoro-3-(trifluoromethyl)phenyl]-2,3,6,9-tetrahydro-7-methyl-methyl ester 1,1,4,4-tetraoxide;

5H-1,4-Dithiepino[6,5-b]pyridine-8-carboxylic acid, 9-(2,3-difluorophenyl)-2,3,6,9-tetrahydro-7-methyl-methyl ester 1,1,4,4-tetraoxide;

5H-1,4-Dithiepino[6,5-b]pyridine-8-carboxylic acid, 2,3,6,9-tetrahydro-7-methyl-9-(2-nitrophenyl)-methyl ester 1,1,4,4-tetraoxide;

5H-1,4-Dithiepino[6,5-b]pyridine-8-carboxylic acid, 9-[2-fluoro-3-(trifluoromethyl)phenyl]-2,3,6,9-tetrahydro-7-methyl-3-methylene-methyl ester 1,1,4,4-tetraoxide;

5H-1,4-Dithiepino[6,5-b]pyridine-8-carboxylic acid, 9-[2-fluoro-3-(trifluoromethyl)phenyl]-2,3,6,9-tetrahydro-7-methyl-3-methylene-2-[methyl (phenylmethyl)aimino]ethyl ester 1,1,4,4-tetraoxide;

5H-1,4-Dithiepino[6,5-b]pyridine-8-carboxylic acid, 9-[2-fluoro-3-(trifluoromethyl)phenyl]-2,3,6,9-tetrahydro-3-(hydroxymethyl)-7-methyl-methyl ester 1,1,4,4-tetraoxide;

5H-1,4-Dithiepino[6,5-b]pyridine-8-carboxylic acid, 9-[2-fluoro-3-(trifluoromethyl)phenyl]-2,3,6,9-tetrahydro-3-(hydroxymethyl)-7-methyl-2-[methyl (phenylmethyl)amino]ethyl ester 1,1,4,4-tetraoxide;

5H-1,4-Dithiepino[6,5-b]pyridine-8-carboxylic acid, 2,3,6,9-tetrahydro-3-(hydroxymethyl)-7-methyl-9-(3- nitrophenyl)-2-[methyl(phenylmethyl)amino]ethyl ester 1,1,4,4-tetraoxide;

2H,6H-1,5-Dithiocino[3,2-b]pyridine-9-carboxylic acid, 3,4,7,10-tetrahydro-8-methyl-10-(3-nitrophenyl)-2-[methyl(phenylmethyl)amino]ethyl ester 1,1,5,5-tetraoxide;

2H,6H-1,5-Dithiocino[3,2-b]pyridine-9-carboxylic acid, 10-[2-fluoro-6-(trifluoromethyl)phenyl]-3,4,7,10-tetrahydro-8-methyl-2-[methyl(phenylmethyl)amino]ethyl ester 1,1,5,5-tetraoxide;

2H,6H-1,5-Dithiocino[3,2-b]pyridine-9-carboxylic acid, 3,4,7,10-tetrahydro-8-methyl-10-(pentafluorophenyl)-2-[methyl(phenylmethyl)amino]ethyl ester 1,1,5,5-tetraoxide;

2H,6H-1,5-Dithiocino[3,2-b]pyridine-9-carboxylic acid, 10-[2-fluoro-3-(trifluoromethyl)phenyl]-3,4,7,10-tetrahydro-8-methyl-2-[methyl(phenylmethyl)amino]ethyl ester 1,1,5,5-tetraoxide;

2H,6H-1,5-Dithiocino[3,2-b]pyridine-9-carboxylic acid, 10-(2-chlorophenyl)-3,4,7,10tetrahydro-8-methyl-2-[methyl(phenylmethyl)amino]ethyl ester 1,1,5,5-tetraoxide;

2H,6H-1,5-Dithiocino[3,2-b]pyridine-9-carboxylic acid, 3,4,7,10-tetrahydro-8-methyl-10-(2-nitrophenyl)-2-[methyl(phenylmethyl)amino]ethyl ester 1,1,5,5-tetraoxide;

4H-1,3-Dithiocino[5,4-b]pyridine-7-carboxylic acid, 8-[2-fluoro-3-(trifluoromethyl)phenyl-]-5,8-dihydro-6-methyl-2-[methyl(phenylmethyl)amino]ethyl ester 1,1,3,3-tetraoxide; and 4H-1,3-Dithiocino[5,4-b]pyridine-7-carboxylic acid, 8-(2-chlorophenyl)-5,8-dihydro-6-methyl-2-[methyl(phenylmethyl)amino]ethyl ester 1,1,3,3-tetraoxide.

This invention also provides soft drug analogs of the compounds of Formula I. These soft drugs are characterized by a chemically labile moiety bound to the ester group in turn bound to the dihydropyridine ring structure. The soft drugs permit the instant drugs to exert their effect locally, and to subsequently be metabolized in the blood stream, thereby reducing unwanted systemic effects (e.g. low blood pressure). Use of such soft drug analogs permits the administration of greater doses of the claimed dihydropyridine compounds without subjecting the subject to intolerable levels of unwanted systemic effects.

Specifically, this invention provides compounds of Formula II,

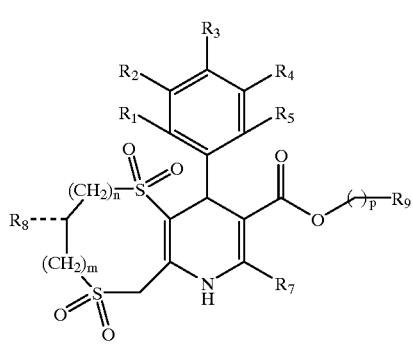

II or a pharmaceutically acceptable salt thereof, wherein
(a) $R_1$, $R_2$, $R_3$, $R_4$ and $R_5$ are independently selected from the group consisting of H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl, and oxadiazole (formed by $R_1$ and $R_2$);

(b) $R_7$ is selected from the group consisting of H, amino, alkyl, aryl, trifluoromethyl, alkoxymethyl, 2-thieno and 3-thieno;

(c) $R_8$ is connected to the bis-sulfone ring via a single or double bond, as applicable, and is selected from the group consisting of H, alkylhydroxy, alkenyl, amino, phenyl, benzyl, $C_{1-8}$ straight or branched alkyl, trifluoromethyl, alkoxymethyl, $C_{3-7}$ cycloalkyl, substituted benzyl, formyl, acetyl, t-butyloxy carbonyl, propionyl, substituted alkyl and $R'''CH_2C=O$, wh(erein (i) said substituted benzyl is substituted with halogen, trifluoromethyl, $C_{1-8}$ straight and/or branched alkyl or $C_{1-8}$ alkoxy, (ii) said s,ubstituted alkyl is substituted with amino, dialkyl amino, $C_{1-8}$ alkoxy, hydroxy and/or halogen, and (iii) R''' is amino, dialkyl amino, $C_{1-8}$ alkoxy, hydroxy or halogen;

(d) $R_9$ is selected from -alkyl-OH, alkylamine, lactone, cyclic carbonate, alkyl-substituted cyclic carbonate, aryl-substituted cyclic carbonate, -aryl-C(O)OR', -alkyl-aryl-C(O)OR', -alkyl-OC(O)R', -alkyl-C(O)R', -alkyl-C(O)OR', -alkyl-N(R'')C(O)R', and -alkyl-N(R'')C(O)OR', wherein
R' and R'' are independently selected from the group consisting of hydrogen, amino, alkyl, aryl, aryl-fused cycloalkyl, and heterocyclyl, the amino, alkyl, aryl, aryl-fused cycloalkyl, and heterocyclyl being optionally substituted with halogen, cyano, $NO_2$, lactone, amino, alkylamino, aryl-substituted alkylamino, amide, carbamate, carbamoyl, cyclic carbonate, alkyl, halogen-substituted alkyl, arylalkyl, alkoxy, heterocyclyl and/or aryl (the aryl being optionally substituted with OH, halogen, cyano, $NO_2$, alkyl, amino, dimethylamino, alkoxy, alkylsulfonyl, $C_{1-4}$ carboalkoxy, alkylthio and/or trifluoromethyl);

(e) m, n, and their sum are each an integer from 0 to 4; and
(f) p is an integer from 0 to 4.

Each of the preferred embodiments of the compounds of Formula I set forth above is also contemplated as an embodiment of the compounds of Formula II. In addition, in a preferred embodiment of the compounds of Formula II, $R_9$ is -aryl-alkyl-OC(O)R', -alkyl-N(R'')C(O)R', or -alkyl-OC(O)R' wherein R' and R'' are as described above.

The following compounds are also preferred embodiments of the present invention:

5H-[1,4]dithiepino[6,5-b]pyridine-8-carboxylic acid, 9-(2-chloro-6-fluorophenyl)-2,3,6,9-tetrahydro-7-methyl-, 2-[[(1,1-dimethylethoxy)carbonyl]amino] ethyl ester, 1,1,4,4-tetraoxide;

5H-[1,4]dithiepino[6,5-b]pyridine-8-carboxylic acid, 9-(2-chloro-6-fluorophenyl)-2,3,6,9-tetrahydro-7-methyl-, 2-[[(1,2,3,4-tetrahydro-2-naphthalenyl) carbonyl]oxy]ethyl ester, 1,1,4,4-tetraoxide;

5H-[1,4]dithiepino[6,5-b]pyridine-8-carboxylic acid, 9-(2-chloro-6-fluorophenyl)-2,3,6,9-tetrahydro-7-methyl-, 2-[(cycloheptylcarbonyl)oxy]ethyl ester, 1,1,4,4-tetraoxide;

5H-[1,4]dithiepino[6,5-b]pyridine-8-carboxylic acid, 9-(2-chloro-6-fluorophenyl)-2,3,6,9-tetrahydro-7-methyl-, 2-[[4-(1-methylethoxy)benzoyl]oxy]ethyl ester, 1,1,4,4-tetraoxide;

5H-[1,4]dithiepino[6,5-b]pyridine-8-carboxylic acid, 9-(2,3-dichlorophenyl)-2,3,6,9-tetrahydro-7-methyl-, 2-(2-methyl-1-oxopropoxy)ethyl ester, 1,1,4,4-tetraoxide; and 2H,6H-[1,5]dithiocino[3,2-b]pyridine-9-carboxylic acid, 10-(2-chloro-6-fluorophenyl)-3,4,7,10-tetrahydro-8-methyl-, 2-[[4-(1-methylethoxy)benzoyl]oxy]ethyl ester, 1,1,5,5-tetraoxide.

Unless specified otherwise, the term "alkyl" refers to a straight, branched or cyclic sub.,tituent consisting solely of carbon and H with no unsaturation. The term "alkoxy" refers to O-alkyl where alkyl is as defined. Aryl substituents inclue, for example, phenyl, naphthyl, diphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl, —(CH$_2$)$_2$N(CH$_3$)CH$_2$PH, —CH$_2$CH$_2$—N(Me)—CH$_2$— heteroaryl and the like. The term "halo" means fluoro, chloro, bromo and iodo. The symbol "Ph" refers to phenyl. "Independently" means that when there are more than one substituent, the substitutents may be different. Dehydrating agents used in preparing the compounds of Formula I in which R$_8$ is alkenyl (e.g., H$_2$C=) include, but are not limited to, sulfuric acid and acetic anhydride.

The compounds of the instant invention are asymmetric in the dihydropyridine ring at the 4-position and thus exist as optical antipodes. As such, all possible opticail isomers, antipodes, enantiomers, and diastereomers resulting from additional asymmetric centers that may exist in optical antipodes, racemates and racemic mixtures thereof are also part of this invention. The antipodes can be separated by methods known to those skilled in the art such as, for example, fractional recrystallization of diastereomeric salts of enantiomerically pure acids. Alternatively, the antipodes can be separated by chromatography in a Pirkle type column.

As used herein, the phrase "pharmaceutically acceptable salt" means a salt of the free base which possesses the desired pharmacological activity of the free base and which is neither biologically nor otherwise undesirable. These salts may be derived from inorganic or organic acids. Examples of inorganic acids are hydrochloric acid, nitric acid, hydrobromic acid, sulfuric acid, and phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicyclic acid and the like.

The instant compounds can be prepared using readily available starting materials and reaction steps well known in the art (Edema et al., J. Org. Chem. 58: 5624–7, 1993; Howard et al., J. Amer. Chem. Soc. 82:158–64, 1960).

This invention also provides a pharmaceutical composition comprising one of the instant compounds and a pharmaceutically acceptable carrier.

Pharmaceutical compositions containing a compound of the present invention as the active ingredient in intimate admixture with a pharmaceutical carrier can be prepared according to conventional pharmaceutical techniques. The carrier may take a wide variety of forms depending on the form of preparation desired for administration, such as systemic administration including but not limited to intravenous, oral, nasal or parenteral. In preparing the compositions in oral dosage form, any of the usual pharmaceutical carriers may be employed, such as water, glycols, oils, alcohols, flavoring agents, preservatives, coloring agents, syrup and the like in the case of oral liquid preparations (for example, suspensions, elixirs and solutions), and carriers such as starches, sugars, diluents, granulating agents, lubricants, binders, disintegrating ;agents and the like in the case of oral solid preparations (for example, powders, capsules and tablets).

In one embodiment, the compounds of the instant invention are administered by inhalation. For inhalation administration, the compounds can be in a solution intended for administration by metered dose inhalers, or in a form intended for a dry powder inhaler or insufflator. More particularly, the instant compounds can be conveniently delivered in the form of an aerosol spray from a pressurized container, a pack or a nebuliser with the use of a suitable propellant, e.g., dichlorodifluoromethane, trichlorofluoromethane, dichlorotetrafluoroethane, carbon dioxide or other suitable gas. The dosage unit may be determined by providing a valve to deliver a metered amount. Capsules and cartridges made of a pharmaceutically acceptable material such as gelatin for use in an inhaler or insufflator can be formulated to contain a powder mix of the compound and a suitable powder base such as lactose or starch.

Because of thei ease of administration, tablets and capsules represent an advantageous oral dosage unit form wherein solid pharmaceutical carriers are employed. If desired, tablets can be sugar-coated or enteric-coated by standard techniques. For parenterals, the carrier will usually comprise sterile water, though other ingredients to aid solubility or to act as preservatives can be included. Injectable (suspensions can also be prepared, wherein appropriate liquid carriers, suspending agents and the like are employed. The instant compounds can also be administered in the form of an aerosol, as discussed above.

In one embodiment, the instant pharmaceutical composition contains a per dosage unit (e.g., tablet, capsule, powder, injection, teaspoonful and the like) of from about 0.001 to about 100 mg/kg, and preferably from about 0.01 to about 20 mg/kg of the instant compound.

The compounds of the present invention inhibit the uptake of calcium ions into smooth muscle cells, and therefore act to relax or prevent calcium ion-mediated contraction of smooth muscle tissue.

Thus, this invention further provides a method of treating a subject suffering from a disorder whose alleviation is mediated by the reduction of calcium ion influx into cells whose actions contribute to the disorder, which method comprises administering to the subject a therapeutically effective dose of the instant pharmaceutical composition. By way of example, in a subject suffering from asthma, the subject's airways are constricted due to inflammation of airway smooth muscle cells ("SMC's"). Reducing the calcium influx into the SMC's, whose action (i.e., inflammation) contributes to the disorder, would be expected to alleviate the disorder.

This invention still further provides a method of inhibiting in a subject the onset of a disorder whose alleviation is mediated by the reduction of calcium ion influx into cells whose actions contribute to the disorder, which method comprises administering to the subject a prophylactically effective dose of the instant pharmaceutical composition.

In one embodiment, the disorder is selected from the group consisting of hypersensitivity, allergy, asthma, bronchospasm, dysmenorrhea, esophageal spasm, glaucoma, premature labor, a urinary tract disorder, a gastrointestinal motility disorder and a cardiovascular disorder. In the preferred embodiment, the disorder is asthma. The cardiovascular disorder can be, for example, hypertension, ischemia, angina, congestive heart failure, myocardial infarction or stroke.

As used herein, "treating" a disorder means eliminating or otherwise ameliorating the cause and/or effects thereof. "Inhibiting" the onset of a disorder means preventing, delaying or reducing the likelihood of such onset.

The term "subject" includes, without limitation, any animal or artificially modified animal. In the preferred embodiment, the subject is a human.

Methods are known in the art for determining therapeutically and prophylactically effective doses for the instant pharmaceutical composition. The effective dose for administering the pharmaceutical composition to a human, for example, can be determined mathematically from the results of animal studies.

This invention further provides an apparatus for administering to a subject the instant pharmaceutical composition, comprising a container and the pharmaceutical composition therein, whereby the container has a means for delivering to the subject a therapeutic and/or prophylactic dose of the pharmaceutical composition. In the preferred embodiment, the apparatus is an aerosol spray device for treating and/or preventing asthma via topical respiratory administration.

This invention still further provides a process for preparing the compounds of Formula I,

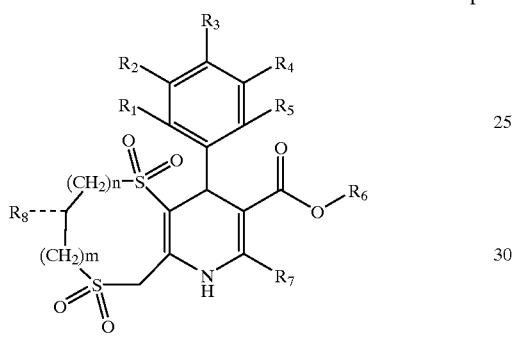

I wherein m, n, and their sum are each an integer from 1 to 4, which process comprises the steps of (a) reacting the compound of Formula 1a with the compound of Formula 1b

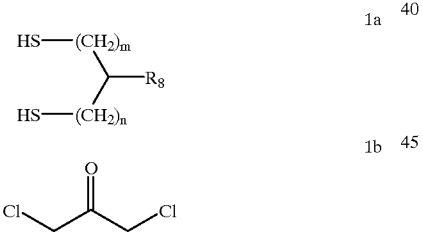

1a

1b to form the compound of Formula 1c;

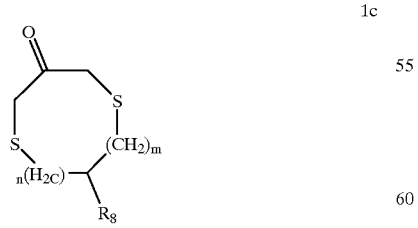

1c (b) reacting the compound of Formula 1 c with m-chloroperoxybenzoic acid to form the compound of Formula 1d; and

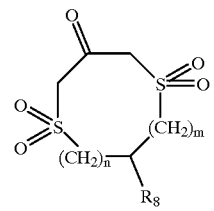

1d (c) reacting the comtpound of Formula 1d with the compounds of Formulae 1e and 1f

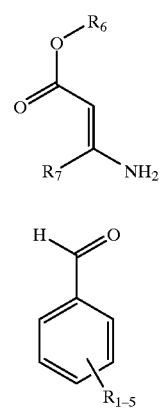

1e

1f to form the compound of Formula I. In one embodiment of this process, $R_8$ of the compound of Formula I is a methylene group formed from a methylol group using a dehydrating agent.

Finally, this invention provides a process of preparing the compounds of Formula II,

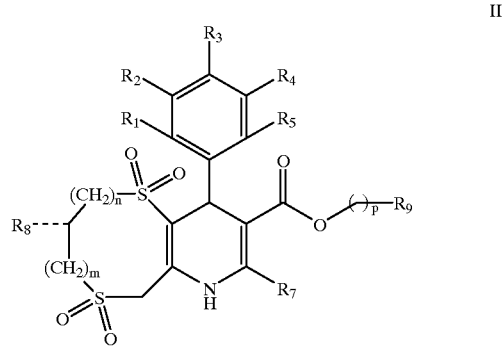

II which process comprises the steps of (a) reacting the compound of Formula 3a' with formic acid to form the compound of Formula 3b'; and

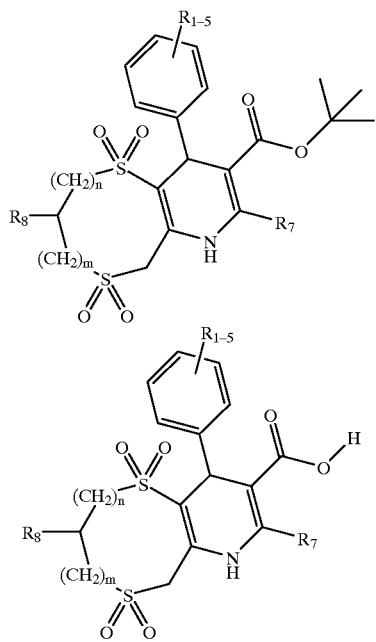

(b) reacting the compound of Formula 3b with $R_9Br$ or $R_9Cl$ to form the compound of Formula II.

In one embodiment of this process, $R_7$ of the compound of Formula II is methyl.

This invention will be better understood by reference to the Experimental Details that follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

Experimental Details

A. Schemes and Syntheses

Scheme I, wherein $R_8$ is as described above, shows the preparation of the key intermediate 1c in the synthesis of Formula I where $n+m\neq 0$. Howard et al. (J. Amer. Chem. Soc. 82, 158–164, 1960) describes in detail how to prepare intermediate 1c where $n+m=0$.

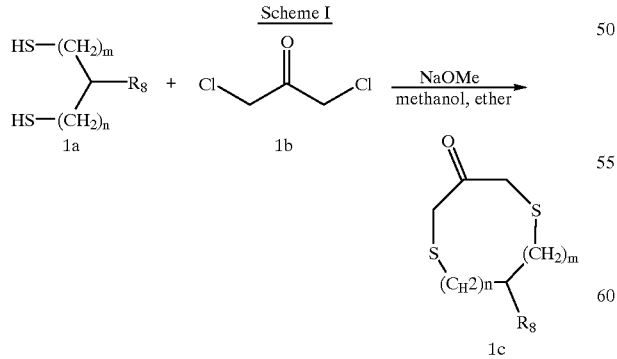

The compounds of Formula I can be made in accordance with the following general procedures outlined in Scheme II wherein $R_1$, $R_2$, $R_3$, $R_4$, $R_5$, $R_6$, $R_7$ and $R_8$ are as described above:

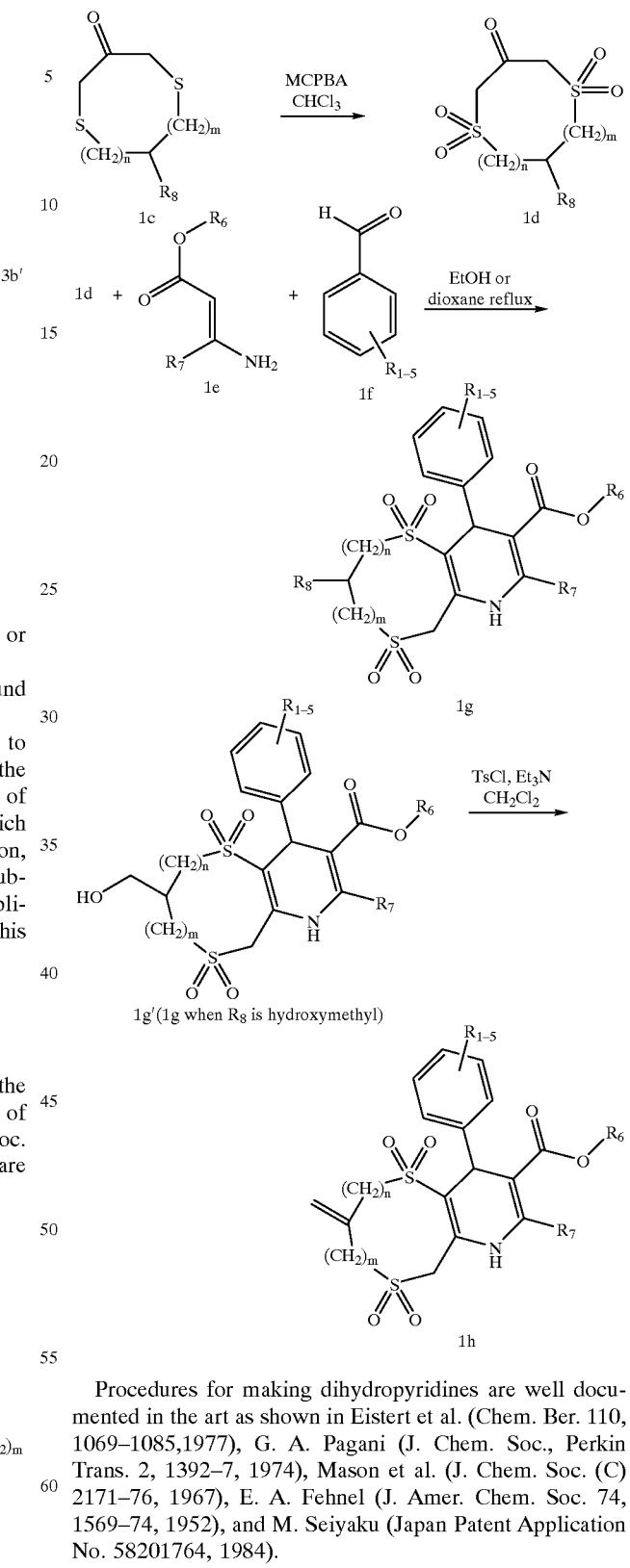

Procedures for making dihydropyridines are well documented in the art as shown in Eistert et al. (Chem. Ber. 110, 1069–1085, 1977), G. A. Pagani (J. Chem. Soc., Perkin Trans. 2, 1392–7, 1974), Mason et al. (J. Chem. Soc. (C) 2171–76, 1967), E. A. Fehnel (J. Amer. Chem. Soc. 74, 1569–74, 1952), and M. Seiyaku (Japan Patent Application No. 58201764, 1984).

The compounds of Formula II can be made in accordance with Schemes III and IV, wherein compounds of IIb and IIe are different subsets of the compounds of IIa, and $R_{1-8}$ are as described above:

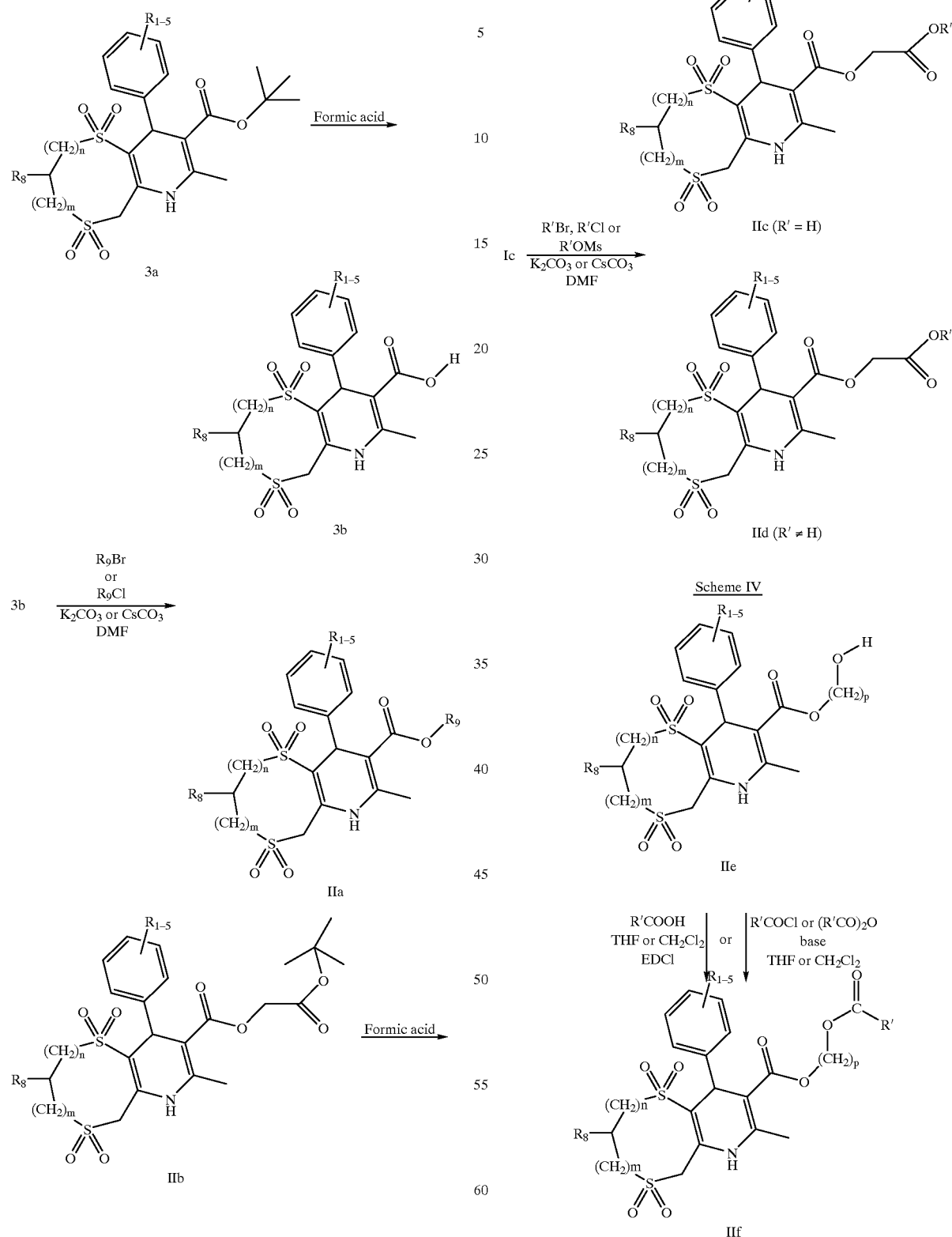

The Examples below describe in greater detail the chemical syntheses of representative compounds of the present invention. The rest of the compounds disclosed herein can be prepared similarly in accordance with one or more of these methods. No attempt has been made to optimize the yields obtained in theses syntheses, and it would be clear to one skilled in the art that variations in reaction times, temperatures, solvents, and/or reagents could be used to increase such yields.

Tables 1–5 set forth the mass spectra data, the inhibition of nitrendipine binding and inhibition of calcium-dependent smooth muscle contraction for selected compounds of Formula I.

TABLE 1

Mass Spectra Data and Calcium Channel Antagonist Activity for Compounds 1–19

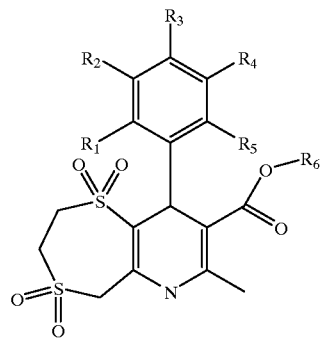

| Compound No. | $R_1$ | $R_2$ | $R_3$ | $R_4$ | $R_5$ | $R_6$ | MS ci (M + 1) | Nitrendipine Binding Assay $IC_{50}$ μM | Trachea $IC_{50}$ μM |
|---|---|---|---|---|---|---|---|---|---|
| 1 | Cl | H | H | H | F | $(CH_2)_2N(CH_3)CH_2PH$ | 583.2 | 0.074 | 0.65 |
| 2 | Cl | H | H | H | F | $(CH_2)_2N(CH_3)CH_2PH$ | 583.2 | 0.043 | 0.66 |
| 3 | Cl | H | H | H | F | $(CH_2)_2N(CH_3)CH_2PH$ | 583.2 | 160 | |
| 4 | Cl | H | H | H | OH | $(CH_2)_2N(CH_3)CH_2PH$ | 581.1 | 0.39 | |
| 5 | F | H | H | H | $CF_3$ | $(CH_2)_2N(CH_3)CH_2PH$ | 617.4 | 0.012 | |
| 6 | H | H | H | H | Cl | $(CH_2)_2N(CH_3)CH_2PH$ | 565.2 | 0.045 | |
| 7 | H | H | H | $CF_3$ | F | $(CH_2)_2N(CH_3)CH_2PH$ | 617.3 | 0.018 | |
| 8 | H | H | H | $NO_2$ | H | $(CH_2)_2N(CH_3)CH_2PH$ | 576.1 | 0.043 | |
| 9 | H | F | F | F | H | $(CH_2)_2N(CH_3)CH_2PH$ | 585.1 | 0.013 | |
| 10 | H | F | F | F | H | $(CH_2)_2N(CH_3)CH_2$thiophene | 591.2 | 0.024 | |
| 11 | Cl | H | H | H | F | Me | 450.0 | 0.091 | |
| 12 | Cl | H | H | $NO_2$ | H | Me | 499 (M + 23) | 0.261 | |
| 13 | F | F | F | F | F | Me | 488.0 | 0.027 | |
| 14 | F | H | H | H | F | Me | 433.9 | 0.259 | |
| 15 | H | H | H | H | Cl | Me | 432.0 | 0.061 | |
| 16 | H | H | H | H | F | Me | 416.0 | 0.265 | |
| 17 | H | H | H | $CF_3$ | F | Me | 484.0 | 0.02 | |
| 18 | H | H | H | F | F | Me | 434.0 | 0.068 | |
| 19 | H | H | H | H | $NO_2$ | Me | 465 (M + 23) | 0.21 | |

EXAMPLE 1

5H-1,4-Dithiepino[6,5-b]pyridine-8-carboxylic acid, 9-(2-chloro-6-fluorophenyl)-2,3,6,9-tetrahydro-7-methyl-2-[methyl(phenylmethyl)amino]ethyl ester 1,1,4,4-tetraoxide, its enantiomers, and phosphate salts thereof Compound 1

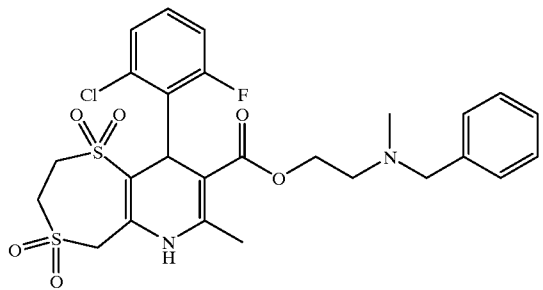

1,1,4,4-tetraoxide-1,4-Dithiepan-6-one (5.0 g, 0.0236 mol), 2-chloro-6-fluorobenzaldehyde (3.7 g, 0.0236 mol), 2-(N-methyl-N-methylphenyl)aminoethyl 3-aminocrotonate (5.9 g, 0.0236 mol) and ethanol (50 mL) were heated to 80° C. for 24 hours. The solvent was removed in vacuo and the resulting oil purified on $SiO_2$ eluting with 50% hexanes in ethyl acetate. The product (Compound 1) was isolated as a white solid (3.9 g, 28% yield).

Compound 2

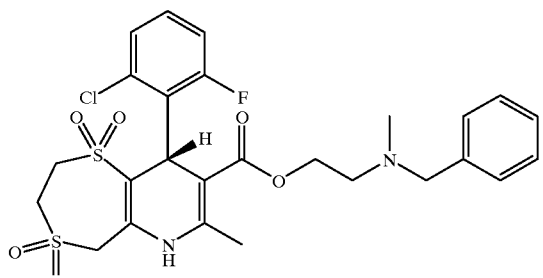

and

Compound 3

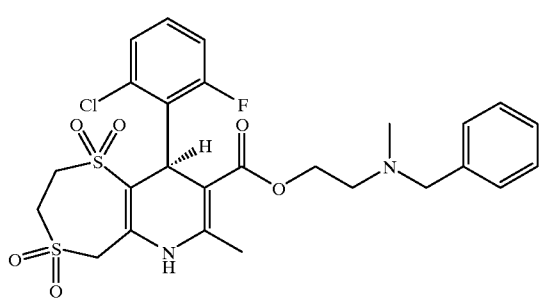

Compound 1 (5.0 g, 0.0085 mol) was separated into its two enantiomers (>97ee) using chiral chromatography, eluting with 0.05% diethylamine in ethanol. The respective phosphate salts were prepared by dissolving each (2.1 g, 0.0036 mol) in ethyl acetate (15 mL), and a solution of phosphoric acid 85% (0.41 g, 0.0036 mol) in ether (100 mL) was added dropwise. After stirring 1 hour, the reaction was diluted to a volume of 200 mL. After 4.5 hours the (resulting precipitate was filtered washed with ether, and dried to give 2.3 g of the phosphate salt (Compounds 2 and 3, which are 5H-1,4-Dithiepino[6,5-b]pyridine-8-carboxylic acid, 9-(2-chloro-6-fluorophenyl)-2,3,6,9-tetrahydro-7-methyl-2-[methyl(phenylmethyl)amino]ethyl ester 1,1,4,4-tetraoxide, (9R), and 5H-1,4-Dithiepino[6,5-b]pyridine-8-carboxylic acid, 9-(2-chloro-6-fluorophenyl)-2,3,6,9-tetrahydro-7-methyl-2-[methyl(phenylmethyl)amino]ethyl ester 1,1,4,4-tetraoxide, (9S)). The correlation of R and S stereochemistry with respect to Compounds 2 and 3 has not been established. Peak 1 Calc'd. for $C_{26}H_{28}ClFN_2O_6S_2 \cdot H_2O \cdot H_3O_4P$: C, 44.67; H, 4.76; N, 4.01; P, 4.43. Found: C, 44.44; H, 4.55; N, 3.78; P, 4.30. Peak 2 Calc'd. for $C_{26}H_{28}ClFN_2O_6S_2 \cdot H_2O \cdot H_3O_4P$: C, 44.67; H, 4.76; N 4.43. Found: C, 44.68; H, 4.49; N, 3.85; P, 4.58.

EXAMPLE 2

5H-1,4-Dithiepino[6,5-b]pyridine-8-carboxylic acid, 2,3,6,9-tetrahydro-7-methyl-9-(3,4,5-trifluorophenyl)-2-[methyl(2-thienylmethyl)amino]ethyl ester 1,1,4,4-tetraoxide Compound 10

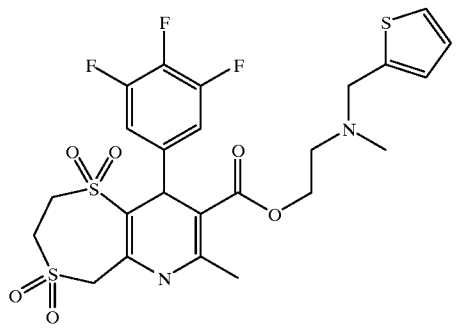

1,1,4,4-tetraoxide-1,4-Dithiepino-6-one (0.3 g, 0.0014 mol), 3,4,5-trifluorobenzaldehyde (0.22 g, 0.0014 mol), 2-N-methyl-(N-methyl-2-thiophene)aminoethyl crotonate (0.36 g, 0.0014 mol), ammonium acetate (0.21 g), triethylamine (2.0 mL) and dioxane (7 mL) were heated to 100° C. for 48 hours. The solvent was removed in vacuo and the resulting oil purified on $SiO_2$ eluting with 40% ethyl acetate in hexanes. The product was dissolved in ether and hydrochloric acid gas was bubbled through the solution. The resulting precipitate (Compound 10) was filtered to give a white solid (0.118 g, 13% yield).

TABLE 2

Mass Spectra Data and
Calcium Channel Antagonist Activity for Compounds 20 and 21

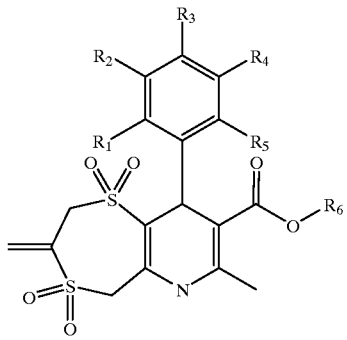

| Compound No. | $R_1$ | $R_2$ | $R_3$ | $R_4$ | $R_5$ | $R_6$ | MS ci (M + 1) | Nitrendipine Binding Assay $IC_{50}$ μM |
|---|---|---|---|---|---|---|---|---|
| 20 | H | H | H | $CF_3$ | F | Me | 496.3 | 0.021 |
| 21 | H | H | H | $CF_3$ | F | $(CH_2)_2N(CH_3)CH_2PH$ | 629.0 | 0.038 |

EXAMPLE 3

5H-1,4-Dithiepino[6,5-b]pyridine-8-carboxylic acid, 9-[2-fluoro-3-(trifluoromethyl)phenyl]-2,3,6,9-tetrahydro-7-methyl-3-methylene-methyl ester 1,1,4,4-tetraoxide Compound 20

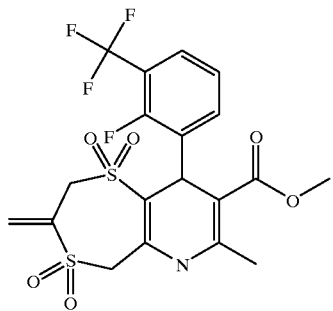

5H-1,4-Dithiepino[6,5-b]pyridine-8-carboxylic acid, 9-[2-fluoro-3-(trifluoromethyl)phenyl]-2,3,6,9-tetrahydro-3-(hydroxymethyl)-7-methyl-methyl ester 1,1,4,4-tetraoxide) (Compound 22, 0.33 g, 0.643 mM), tosyl chloride (0.24 g, 0.643 mM) and triethylamine (0.13 g, 1.29 mM) were refluxed in $CHCl_3$ (50 mL) for 16 hours. The cooled mixture was washed with water (2×20 mL) and dried over $MgSO_4$. After evaporation of the solvent in vacuo, the resulting oil was purified on $SiO_2$ eluting with 50% ethyl acetate in hexanes. The product (Compound 20) was obtained as a colorless solid (0.158 g, 49% yield).

TABLE 3

Mass Spectra Data and
Calcium Channel Antagonist Activity for Compounds 22–24

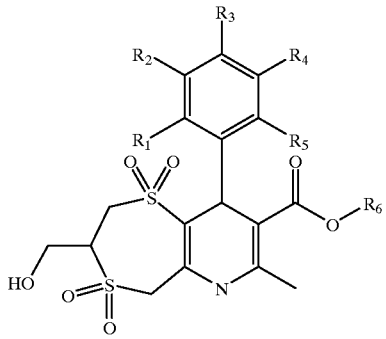

| Compound No. | $R_1$ | $R_2$ | $R_3$ | $R_4$ | $R_5$ | $R_6$ | MS ci (M + 1) | Nitrendipine Binding Assay $IC_{50}$ μM |
|---|---|---|---|---|---|---|---|---|
| 22 | H | H | H | $CF_3$ | F | Me | 514.2 | 0.193 |
| 23 | H | H | H | $CF_3$ | F | $(CH_2)_2N(CH_3)CH_2PH$ | 647.3 | 0.215 |
| 24 | H | H | H | $NO_2$ | H | $(CH_2)_2N(CH_3)CH_2PH$ | 606.4 | 0.337 |

EXAMPLE 4

5H-1,4-Dithiepino[6,5-b]pyridine-8-carboxylic acid, 9-[2-fluoro-3-(trifluoromethyl)phenyl]-2,3,6,9-tetrahydro-3-(hydroxymethyl)-7-methyl-methyl ester 1,1,4,4-tetraoxide

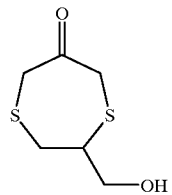

2-hydroxymethyl-1, 4-Dithiepan-6-one

Hydroxymethylethanedithiol (20.0 g, 0.161 mol) was dissolved in 120 mL of 21% sodium ethoxide in ethanol, then diluted to 250 mL with methanol. Dichloroacetone (20.4 g, 0.161 mol) was dissolved in ether and diluted to a total volume of 250 mL. A solution of methanol (100 mL) and ether (100 mL) was stirred at 0° C. in an ice bath. The two solutions of reagents were simultaneously added dropwise over the course of 2.5 hours. The reaction was stirred an additional 30 minutes and poured into ice water containing 1N NaOH (20 mL). The product was extracted into ether (3×200 mL) and filtered to remove some insoluble material. The solution was dried over magnesium sulfate anc evaporated to an oil. The resulting oil was purified on $SiO_2$ eluting with 30% ethyl acetate in hexanes. The product 2-hydroxymethyl-1,4-Dithiepan-6-one was isolated as a colorless oil (10.7 g, 37% yield).

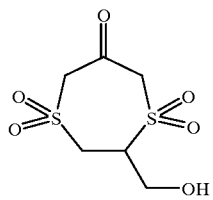

2-hydroxymethyl-1,1,4,4-tetraoxide-1,4-Dithiepan-6-one 2-hydroxymethyl-1,4-Dithiepan-6-one (9.5 g, 0.532 mol) was dissolved in chloroform (750 mL) and stirred at 5° C. MCPBA (m-chloroperoxybenzoic acid; 45.6 g, 0.213 mol) was added portionwise keeping the temperature below 10° C. The mixture was allowed to warm to 25° C. and stirring was continued for 24 hours. The resulting precipitate was filtered and washed twice with $CH_2Cl_2$. Next, the solid was washed with methanol to give 2-hydroxymethyl-1,1,4,4-tetraoxide-1,4-Dithiepan-6-one (9.7 g, 75% yield) as a white solid.

Compound 22

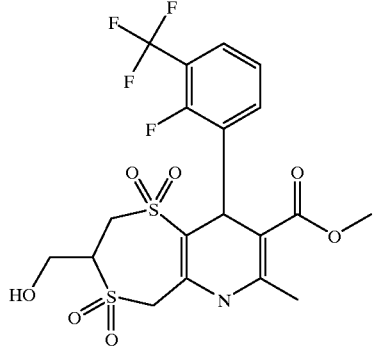

2-hydroxymethyl-1,1,4,4-tetraoxide-1,4-Dithiepan-6-one (0.6 g, 0.0025 mol), 2-fluoro-3-trifluoromethylbenzaldehyde (0.5 g, 0.0025 mol), and methyl 3-aminocrotonate (0.3 g, 0.0025 mol) and dioxane (30 mL) were heated to 110° C. for 40 hours. The solvent was removed in vacuo and the resulting oil purified on $SiO_2$ eluting with 40% hexanes in ethyl acetate. The product (Compound 22) was isolated as a white solid (0.37 g, 28% yield). Anal. Calc'd. for $C_{19}H_{19}F_4NO_7S_2$: C, 44.44; H, 3.73; N, 2.73. Found: C, 44.32; H, 3.78; N, 2.52.

TABLE 4

Mass Spectra Data and
Calcium Channel Antagonist Activity for Compounds 25–30

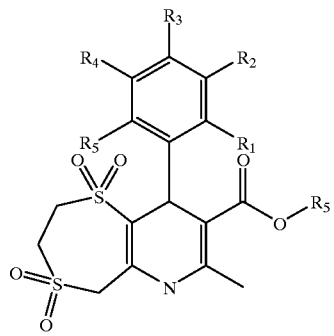

| Compound No. | $R_1$ | $R_2$ | $R_3$ | $R_4$ | $R_5$ | $R_6$ | MS ci (M + 1) | Nitrendipine Binding Assay $IC_{50}$ $\mu M$ | Trachea $IC_{50}$ $\mu M$ |
|---|---|---|---|---|---|---|---|---|---|
| 25 | H | H | H | $NO_2$ | H | $(CH_2)_2N(CH_3)CH_2PH$ | 590.3 | 0.010 | |
| 26 | F | H | H | H | $CF_3$ | $(CH_2)_2N(CH_3)CH_2PH$ | 631.3 | 0.028 | |
| 27 | F | F | F | F | F | $(CH_2)_2N(CH_3)CH_2PH$ | 635.2 | 0.049 | 6.2 |
| 28 | H | H | H | $CF_3$ | F | $(CH_2)_2N(CH_3)CH_2PH$ | 631.3 | 0.053 | |
| 29 | H | H | H | H | Cl | $(CH_2)_2N(CH_3)CH_2PH$ | 579.3 | 0.057 | |
| 30 | H | H | H | H | $NO_2$ | $(CH_2)_2N(CH_3)CH_2PH$ | 647.3 | 0.716 | |

EXAMPLE 5

2H,6H-1,5-Dithiocino[3,2-b]pyridine-9-carboxylic acid, 3,4,7,10-tetrahydro-8-methyl-10-(3-nitrophenyl)-2-[methyl(phenylmethyl)amino]ethyl ester 1,1,5,5-tetraoxide Compound 25

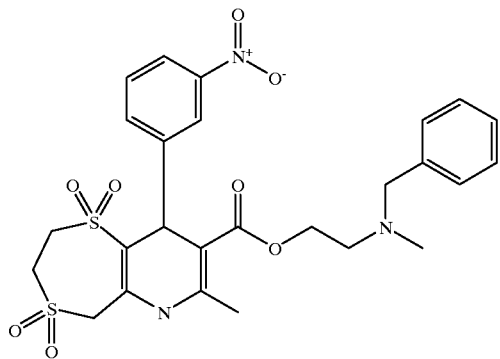

1,1,5,5-tetraoxide-1,5-Dithiocan-3-one (0.3 g, 0.0013 mol), 3-nitrobenzaldehyde (0.2 g, 0.0013 mol), 2-(N-methyl-N-methylphenyl)aminoethyl 3-aminocrotonate (0.33 g, 0.0013 mol) and dioxane (15 mL) were heated to 101° C. for 24 hours. The solvent was removed in vacuo and the resulting oil purified on $SiO_2$ eluting with 50% hexanes in ethyl acetate. The resulting oil was dissolved in ethyl acetate and hydrogen chloride gas was bubbled through the solution. The resulting precipitate was filtered and washed wiih ether. The product was Compound 25 (0.11 g, 13% yield). Anal. Calc'd. for $C_{27}H_{31}N_3O_8S_2$.0.5 $H_2O$. HCl: C, 51.06; H, 5.24; N, 6.62. Found: C, 50.76 H, 5.15; N, 6.44.

TABLE 5

Mass Spectra Data and
Calcium Channel Antagonist Activity for Compounds 31, 32

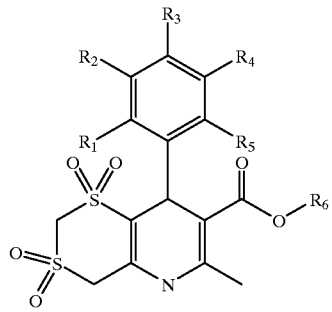

| Compound No. | $R_1$ | $R_2$ | $R_3$ | $R_4$ | $R_5$ | $R_6$ | MS ci (M + 1) | Nitrendipine Binding Assay $IC_{50}$ μM |
|---|---|---|---|---|---|---|---|---|
| 31 | H | H | H | $CF_3$ | F  | $(CH_2)_2N(CH_3)CH_2PH$ | 603.3 | 0.028 |
| 32 | H | H | H | H      | Cl | $(CH_2)_2N(CH_3)CH_2PH$ | 551.3 | 0.039 |

EXAMPLE 6

4H-1,3-Dithiino[5,4-b]pyridine-7-carboxylic acid, 8-[2-fluoro-3-(trifluoromethyl)phenyl]-5,8-dihydro-6-methyl-2-[methyl(phenylmethyl)amino]ethyl ester 1,1,3,3-tetraoxide Compound 31

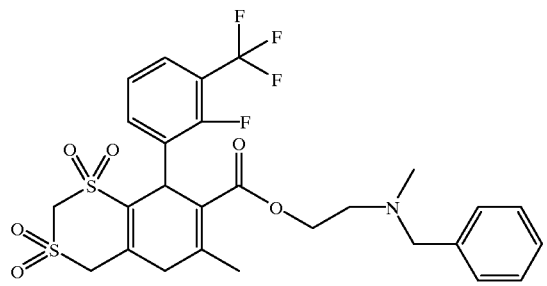

1,1,3,3-tetraoxide-1,3-Dithian-5-one (0.3 g, 0.0015 mol), 2-fluoro-3-trifluoromethylbenzaldehyde (0.29 g, 0.0015 mol), 2-(N-methyl-N-methylphenyl)aminoethyl 3-aminocrotonate (0.38 g, 0.0015) and dioxane (15 mL) were heated to 101° C. for 48 hours. The solvent was removed in vacuo and the resulting oil purified on $SiO_2$ eluting with 50% hexanes in ethyl acetate. The resulting oil was dissolved in ethyl acetate and hydrogen chloride gas was bubbled through the solution. The resulting precipitate was filtered and washed wiih ether (0.14 g, 26% yield). Anal. Calc'd. for $C_{26}H_{26}F_4N_2O_6S_2$. HCl: C, 48.86; H, 4.26; N, 4.38; Found: C, 49.45; H, 4.62; N, 4.34.

EXAMPLE 7

7-methyl-9-[2-fluoro-6-chlorophenyl]-2,3,6,9-tetrahydro-1,1,4,4-tetraoxide 5H-1,4-Dithiepino[6,5-b]pyridine-8-carboxylic acid

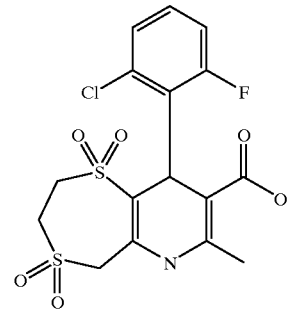

7-methyl-9-[2-fluoro-6-chlorophenyl]-2,3,6,9-tetrahydro-1,1,4,4-tetraoxide 5H-1,4-Dithiepino[6,5-b] pyridine-8-carboxylic acid 1,1-dimethylethyl ester (11.8 g. 0.024 mol) was suspended in 96% formic acid (70 mL) and stirred at 25° C. for 16 hours. The resulting solid was filtered and washed with water followed by an ether wash. The colorless solid was dried under vacuum at 60° C. to gives 8.4 g (81% yield) of 7-methyl-9-[2-fluoro-6-chlorophenyl]-2,3, 6,9-tetrahydro-1,1,4,4-tetraoxide 5H-1,4-Dithiepino[6,5-b] pyridine-8-carboxylic acid.

Tables 6 and 7 below set forth the mass spectra data and the inhibition of nitrendipine binding data for selected compounds of Formula II.

TABLE 6

Mass Spectra Data and
Calcium Channel Antagonist Activity for Compounds 33–98

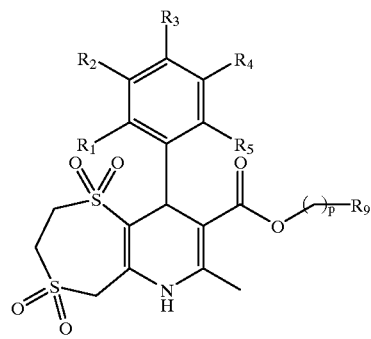

| Compound No. | $R_1$ | $R_2$ | $R_3$ | $R_4$ | $R_5$ | p | $R_9$ | M + 23 or M + 1 | Nitrendipine Binding Assay $IC_{50}$ nM |
|---|---|---|---|---|---|---|---|---|---|
| 33 | F | H | H | H | Cl | 1 | $CH_2OC(O)CH(CH_2CH_3)_2$ | 600 | 13 |
| 34 | Cl | Cl | H | H | H | 1 | $CH_2OC(O)CH(CH_3)_2$ | 588 | 15 |
| 35 | F | H | H | H | Cl | 1 | $CH_2OC(O)$-PH-$OCH(CH_3)_2$ | 664 | 20 |
| 36 | F | H | H | H | Cl | 1 | $CH_2OC(O)(CH_2)_2CH(CH_3)_2$ | 600 | 20 |
| 37 | F | H | H | H | Cl | 1 | $CH_2OC(O)CH(CH_3)CH_2$-PH | 648 | 33 |
| 38 | F | H | H | H | Cl | 1 | $CH_2OC(O)CH_2CH(CH_3)_2$ | 586 | 35 |
| 39 | F | H | H | H | Cl | 1 | $CH_2OC(O)CH(CH_2)_6$ | 626 | 38 |
| 40 | F | H | H | H | Cl | 1 | $CH_2OC(O)$-PH-3-$OCH_3$ | 636 | 41 |
| 41 | F | H | H | H | Cl | 2 | $CH_2OC(O)$-PH | 620 | 43 |
| 42 | F | H | H | H | Cl | 1 | $CH_2OC(O)$-(2-tetrahydronaphthyl) | 660 | 44 |
| 43 | F | H | H | H | Cl | 1 | $CH_2OC(O)$-PH-$CF_3$ | 674 | 48 |
| 44 | F | H | H | H | Cl | 1 | $CH_2OC(O)(CH_2)_2PH$ | 634 | 48 |
| 45 | F | H | H | H | Cl | 1 | -PH-$C(O)OCH_3$ | 606 | 48 |
| 46 | F | H | H | H | Cl | 1 | $CH_2OC(O)$-(2-naphthyl) | 656 | 50 |
| 47 | F | H | H | H | Cl | 1 | $CH_2OC(O)CH_2N(CH_3)CH_2PH$ | 663 | 50 |
| 48 | F | H | H | H | Cl | 1 | $CH_2OC(O)$-PH-4-CN | 631 | 55 |
| 49 | F | H | H | H | Cl | 3 | $CH_2OC(O)$-PH | 634 | 57 |
| 50 | F | H | H | H | Cl | 1 | $CH_2OC(O)$-PH-3-CN | 631 | 61 |
| 51 | F | H | H | H | Cl | 1 | $CH_2OC(O)$-PH | 606 | 62 |
| 52 | F | H | H | H | Cl | 1 | $CH_2OC(O)$-PH-4-$OCH_3$ | 636 | 69 |
| 53 | H | H | H | Cl | Cl | 1 | (4,5-dimethyl-1,3-dioxol-2-one-yl) | 586 | 72 |
| 54 | F | H | H | H | Cl | 1 | $CH_2OC(O)CH_2$-PH-$N(CH_3)_2$ | 663 | 80 |
| 55 | F | H | H | H | Cl | 1 | $CH_2OC(O)CH(CH_2)_5$ | 612 | 100 |
| 56 | F | H | H | H | Cl | 1 | $CH_2OC(O)CH_2$-PH-$N(CH_3)_2$ | 649 | 118 |
| 57 | F | H | H | H | Cl | 1 | $CH_2OC(O)CH(CH_3)_2$ | 572 | 143 |
| 58 | F | H | H | H | Cl | 1 | $CH_2OC(O)CH_2N(CH_3)C(O)PH$ | 677 | 153 |
| 59 | F | H | H | H | Cl | 1 | $C(O)O(CH_2)_2PH$ | 620 | 154 |

TABLE 6-continued

Mass Spectra Data and
Calcium Channel Antagonist Activity for Compounds 33–98

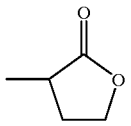

| Compound No. | R₁ | R₂ | R₃ | R₄ | R₅ | p | R₉ | M + 23 or M + 1 | Nitrendipine Binding Assay IC₅₀ nM |
|---|---|---|---|---|---|---|---|---|---|
| 60 | F | H | H | H | Cl | 0 | 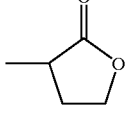 | 542 | 174 |
| 61 | F | H | H | H | Cl | 1 | CH₂OC(O)CH(NHC(O)OC(CH₃)₃) (CH₂)₄NHC(O)OCH₂PH | — | 175 |
| 62 | F | H | H | H | Cl | 2 | CH₂OC(O)CH(CH₃)₂ | 586 | 176 |
| 63 | Cl | Cl | H | H | H | 2 | 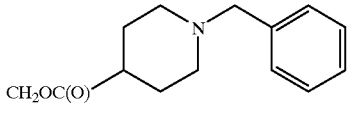 | 586 | 194 |
| 64 | F | H | H | H | Cl | 1 | CH₂OC(O)CH(CH₃)₂ | 572 | 220 |
| 65* | Cl | H | H | H | F | 2 | C(O)OPH | 620 | 276 |
| 66 | F | H | H | H | Cl | 1 | C(O)OCH₂PH | 606 | 279 |
| 67 | Cl | H | H | H | F | 1 | C(O)OPH | 592 | 336 |
| 68 | Cl | H | H | H | F | 2 | CH₂OC(O)CH₃ | 558 | 340 |
| 69 | F | H | H | H | Cl | 1 | C(O)OC(CH₃)₃ | 572 | 356 |
| 70 | F | H | H | H | Cl | 1 | CH₂OC(O)CH(NHCOPH)CH₂PH | 753 | 358 |
| 71 | F | H | H | H | Cl | 1 | 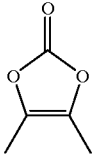 | 703 | 358 |
| 72 | F | H | H | H | Cl | 1 | CH₂OC(O)CH (NHC(O)OC(CH₃)₃)CH(CH₃)₂ | 701 | 405 |
| 73 | F | H | H | H | Cl | 1 | 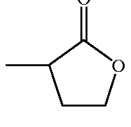 | 570 | 417 |
| 74 | Cl | H | H | H | F | 1 | C(O)O(CH₂)₂N(CH₃)CH₂PH | 663 | 420 |
| 75 | H | H | H | Cl | Cl | 0 |  | 558 | 456 |

TABLE 6-continued

Mass Spectra Data and
Calcium Channel Antagonist Activity for Compounds 33–98

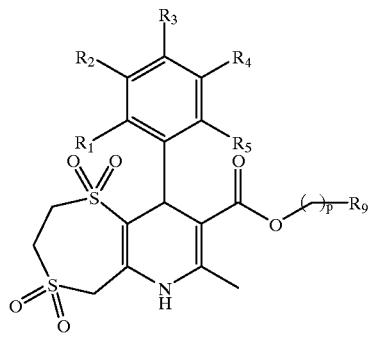

| Compound No. | R₁ | R₂ | R₃ | R₄ | R₅ | p | R₉ | M + 23 or M + 1 | Nitrendipine Binding Assay IC$_{50}$ nM |
|---|---|---|---|---|---|---|---|---|---|
| 76 | F | H | H | H | Cl | 1 | CH₂OC(O)-(3-pyridyl) | 585 | 505 |
| 77 | F | H | H | H | Cl | 1 | CH₂OC(O)CH(N(CH₃)₂)CH₂PH | 677 | 541 |
| 78 | F | H | H | H | Cl | 1 | CH₂OC(O)-(4-pyridyl) | 607 | 760 |
| 79 | F | H | H | H | Cl | 1 | CH₂NHC(O)OC(CH₃)₃ | 601 | 768 |
| 80 | F | H | H | H | Cl | 1 | CH₂OC(O)CH₃ | 544 | 898 |
| 81 | F | H | H | H | Cl | 1 | CH₂OC(O)CH₂NHC(O)OC(CH₃)₂) | 659 | 946 |
| 82 | F | H | H | H | Cl | 1 | CH₂OH | 502 | 1000 |
| 83 | F | H | H | H | Cl | 2 | CH₂OH | 516 | 1208 |
| 84 | F | H | H | H | Cl | 1 | CH₂OC(O)CH₂N(CH₃)₂ | 587 | 1233 |
| 85 | Cl | H | H | H | F | 2 | 3-methyl-γ-butyrolactone | 570 | 1688 |
| 86 | F | H | H | H | Cl | 2 | CH₂OC(O)CH₃ | 558 | 2122 |
| 87 | F | H | H | H | Cl | 1 | CH₂NHC(O)PH | 605 | 2264 |
| 88* | F | H | H | H | Cl | 1 | CH₂OC(O)CH(CH₃)₂ | 572 | 2323 |
| 89 | F | H | H | H | Cl | 1 | CH₂OC(O)C(CH₃)₃ | 586 | 3700 |
| 90 | F | H | H | H | Cl | 1 | C(O)N(CH₂CH₃)₂ | 571 | 4238 |
| 91 | F | H | H | H | Cl | 1 | CH₂NH₂ | 501 | 4841 |
| 92* | F | H | H | H | Cl | 1 | CH₂OC(O)CH(N*H₂)(CH₃)₂ | 601 | 5800 |
| 93 | F | H | H | H | Cl | 1 | C(O)NH₂ | 515 | 6986 |
| 94 | F | H | H | H | Cl | 1 | CH₂OC(O)-(γ-butyrolactone-3-yl) | 614 | 19370 |
| 95 | F | H | H | H | Cl | 1 | CH₂OC(O)(CH₂)₂-piperidinyl | 641 | 49000 |

TABLE 6-continued

Mass Spectra Data and
Calcium Channel Antagonist Activity for Compounds 33–98

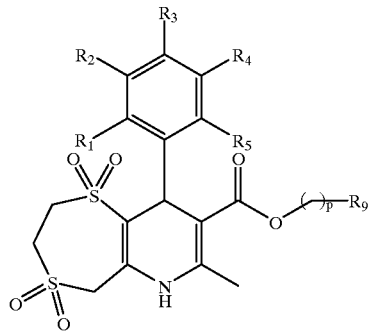

| Compound No. | $R_1$ | $R_2$ | $R_3$ | $R_4$ | $R_5$ | p | $R_9$ | M + 23 or M + 1 | Nitrendipine Binding Assay $IC_{50}$ nM |
|---|---|---|---|---|---|---|---|---|---|
| 96* | F | H | H | H | Cl | 1 | $CH_2OC(O)CH(N*H_2)(CH_2)_4NH_2$ | 608 | 51000 |
| 97 | F | H | H | H | Cl | 1 | $CH_2OC(O)CH_2NH_2$ | 559 | 150000 |
| 98 | Cl | H | H | H | F | 1 | COOH | 516 | 316000 |

*enantiomer/chiral atom

EXAMPLE 8

7-methyl-9-[2-fluoro-13-chlorophenyl]-2,3,6,9-tetrahydro-1,1,4,4-tetraoxide 5H-1,4-Dithiepino[6,5-b]pyridine-8-carboxylic acid 2-(1,1-dimethiylethyloxy)-2-oxoethyl ester (Compound 69)

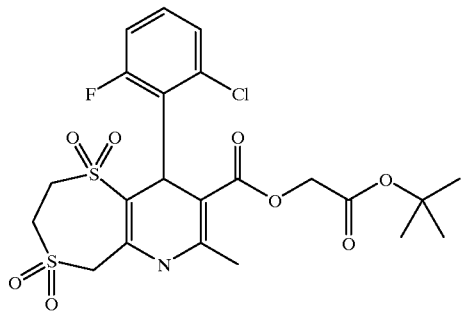

7-methyl-9-[2-fluoro-6-chlorophenyl]-2,3,6,9-tetrahydro-1,1,4,4-tetraoxide 5H-1,4-Dithiepino[6,5-b]pyridine-8-carboxylic acid (1.0 g. 2.29 mmol) was dissolved in DMF (2 mL) and potassium carbonate (0.6 g. 4.34 mmol) was added. After stirring for 15 minutes, bromo t-butyl acetate (0.34 mL 2.29 mmol) was added. After 1 hour, the reaction was diluted with 50 mL of water. This mixture vwas stirred for 15 minutes before filtering the resulting precipitate. This solid was dissolved in 35 mL of ethyl acetate and purified on a bed of silica gel (75 mL) to give pure 7-methyl-9-[2-fluoro-6-chlorophenyl]-2,3,6,9-tetrahydro-1,1,4,4-tetraoxide 5H-1,4-dithiepino[6,5-b]pyridine-8-carboxylic acid 2-(1,1-dimethylethyloxy)-2-oxoethyl ester isolated as a colorless solid (0.81 g. 64% yield).

EXAMPLE 9

7-methyl-9-[2-fluoro-6-chlorophenyl]-2,3,6,9-tetrahydro-1,1,4,4-tetraoxide 5H-1,4-Dithiepino[6,5-b]pyridine-8-carboxylic acid carboxymethyl ester (Compound 98)

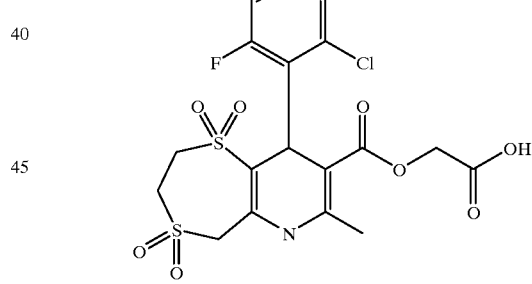

7-methyl-9-[2-fluoro-6-chlorophenyl]-2,3,6,9-tetrahydro-1,1,4,4-tetraoxide 5H-1,4-Dithiepino[6,5-b]pyridine-8-carboxylic acid 2-(1,1-dimethylethyloxy)-2-oxoethyl ester (0.7 g. 1.273 mmol) was suspended in 96% formic acid (6 mL) and stirred at 25° C. for 16 hours. The resulting solid was filtered and washed with water to give a colorless solid. This solid was dissolved in 1N NaOH and washed with ethyl acetate to remove unreacted starting material. The aqueous layer was acidified with 1N HCl and the resulting solid filtered and washed with water and dried. The solid was dried under vacuum at 60° C. to give 0.35 gms (56% yield) of the 7-methyl-9-[2-fluoro-6-chlorophenyl]-2,3,6,9-tetrahydro-1,1,4,4-tetraoxide 5H-1,4-Dithiepino[6,5-b]pyridine-8-carboxylic acid carboxymethyl ester.

EXAMPLE 10

7-methyl-9-[2-fluoro-6-chlorophenyll-2,3,6,9-tetrahydro-1,1,4,4-tetraoxide 5H-1,4-Dithiepino[6,5-b]pyridine-8-carboxylic acid carboxy-2-(1-N-methylbenzylamine)ethyl ester (Compound 74)

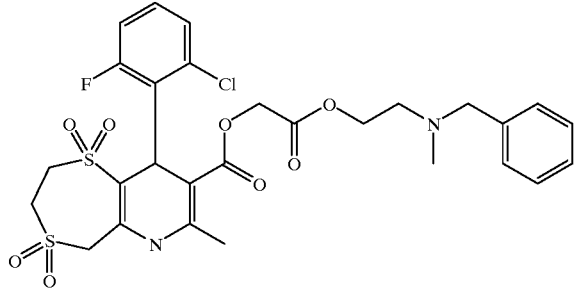

7-methyl-9-[2-fluoro-6-chlorophenyl]-2,3,6,9-tetrahydro-1,1,4,4-tetraoxide 5H-1,4-Dithiepino[6,5-b] pyridine-8-carboxylic acid carboxymethyl ester (0.278 g. 0.563 mmol) was dissolved in DMF (2 mL) and potassium carbonate (0.4 g. 2.894 mmol) was added. After stirring for 15 minutes, N-(2-chloroethyl)-N-methylbenzylamine hydrochloride (0.124g. 0.563 mmol) was added. After heating the reaction to 70° C. for 60 minutes, the reaction was cooled and diluted with 50 mL of water. This mixture was stirred for 15 minutes before extracting into ethyl acetate (2×50 mL). The organic layer was washed with water (3×20 mL) and dried over sodium sulfate. Evaporation of the solvent in vacuo gave an oil which was purified on silica gel eluting with ethyl acetate/hexanes (70/30). Trituration with ether gave pure 7-methyl-9-[2-fluoro-6-chlorophenyl]-2,3,6,9-tetrahydro-1,1,4,4-tetraoxide 5H-1,4-Dithiepino[6,5-b] pyridine-8-carboxylic acid carboxy-2-(1-N-methylbenzylamine)ethyl ester isolated as a colorless solid (0.077g. 21% yield).

EXAMPLE 11

7-methyl-9-[2-fluoro-6-chlorophenyl]-2,3,6,9-tetrahydro-1,1,4,4-tetraoxide 5H-1,4-Dithiepino[6,5-b]pyridine-8-carboxylic acid 3-benzoyloxypropyl ester (Compound 41)

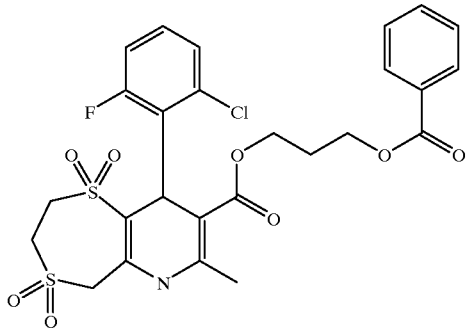

7-methyl-9-[2-fluoro-6-chlorophenyl]-2,3,6,9-tetrahydro-1,1,4,4-tetraoxide 5H-1,4-Dithiepino[6,5-b] pyridine-8-carboxylic acid 3-hydroxypropyl ester (0.179 g. 0.362 mmol), benzoyl chloride (42 uL 0.362 mmol) and triethylamine (0.10 mL)) were stirred in methylene chloride (50 mL) for 16 hours. A second portion of benzoyl chloride (42 uL 0.362 mmol) was added to allow the reaction to go to completion. After 1 hour, the reaction was diluted with methylene chloride (50 mL) and washed with 3N HCl (2×30 mL). The organic layer was dried over sodium sulfate and evaporated in vacuo to give an oil. This resulting oil was purified through a bed of silica gel (40 mL) eluting with methylene chloride to get rid of excess benzoyl chloride. The product was collected by elution with ethyl acetate to give 0.12 g (55% yield) of 7-methyl-9-[2-fluoro-6-chlorophenyl]-2,3,6,9-tetrahydro-1,1,4,4-tetraoxide 5H-1,4-Dithiepino[6,5-b]pyridine-8-carboxylic acid 3-benzoyloxypropyl ester isolated as a colorless solid.

EXAMPLE 12

7-methyl-9-[2-fluoro-6-chlorophenyl]-2,3,6,9-tetrahydo-1,1,4,4-tetraoxide 5H-1,4-Dithiepino[6,5-b]pyridine-8-carboxlic acid 2-[1,2,3,4-tetrahydo-2-napthoyl]oxyethyl ester (Compound 42)

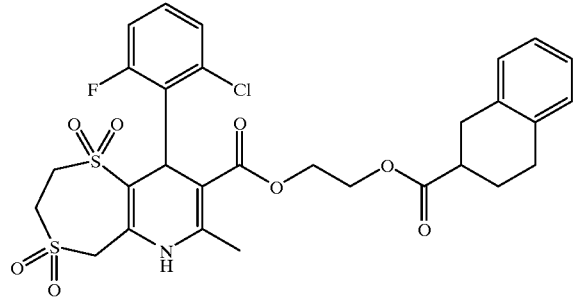

7-methyl-9-[2-fluoro-6-chlorophenyl]-2,3,6,9-tetrahydo-1,1,4,4-tetraoxide 5H-1,4-Dithiepino[6,5-b]pyridine-8-carboxlic acid 2-hydroxyethyl ester (0.3 g. 0.627 mmol) and 1,2,3,4-tetrahydo-2-napthoic acid (0.177 g. 1.00 mmol) was suspended in 6 mL of 2:1 dichloromethane/tetrahydrofuran. To this solution was added 1-(3-Dimethylaminopropyl)-3-ethylcarbodiimide hydrochloride (0.36 g. 1.88 mmol) and dimethyl aminopyridine (0.04g.), stirring at 25° C. for 4 hours. The mixture was diluted with 10 mL of dichloromethane, and was washed with water (1×15 mL), saturated sodium bicarbonate solution (2×15 mL), and brine (1×15 mL). The organic phase was then dried over magnesium sulfate, and filtered through a pad of Celite. Evaporation of the solvent in vacuo afforded an oil which was purified on silica gel eluting with eihyl acetate/hexanes (50/50), to afford 7-methyl-9-[2-fluoro-6-chlorophenyl]-2,3,6,9-tetrahydo-1,1,4,4-tetraoxide 5H-1,4-Dithiepino[6,5-b] pyridine-8-carboxlic acid 2-[1,2,3,4-tetrahydo-2-napthoyl]oxyethyl ester as a pale yellow solid (0.101 g. 26% yield).

EXAMPLE 13

N-Benzyl-N-methyl glycine 2-bromoethyl ester

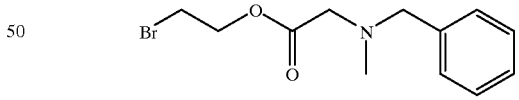

N-Benzyl-N-methyl glycine potassium salt (2.00 g. 11.16 mmol) and 2-Bromo ethanol (2.48 g. 17.86 mmol) was suspended in 20 mL of dichloromethane. To this solution was added 1-(3-Dimethylaminopropyl)-3-ethylcarbodiimide hydrochloride (6.40 g. 33.5 mmol) and 4-dimethylamino) pyridine. (1.00 g.) and the reaction was stirred at 25° C. The mixture was diluted with 40 mL of dichloromethane, and was washed with water (1×60 mL), saturated sodium bicarbonate solution (2×60 and brine (1×60 mL). The organic phase was then dried over magnesium sulfate, and filtered through a pad of Celite. Evaporation of the solvent in vacuo affordedd an oil, which was purified on silica gel eluting with ethyl acetate to afford N-Benzyl-N-methyl glycine 2-bromoethyl ester as an oil (0.70 g. 27% yeild).

TABLE 7

Mass Spectra Data and
Calcium Channel Antagonist Activity for Compounds 99–109

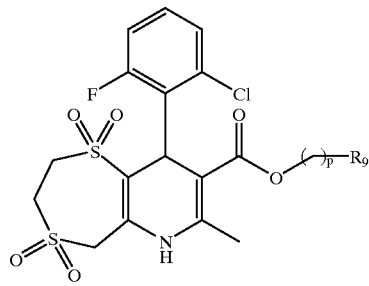

| Compound No. | p | $R_9$ | M + 23 | Nitrendipine Binding Assay $IC_{50}$ nM |
|---|---|---|---|---|
| 99 | 1 | $CH_2OC(O)$-PH-$OCH(CH_3)_2$ | 678 | 40 |
| 100 | 1 | $CH_2OC(O)$-PH-CN | 645 | 49 |
| 101 | 1 | $CH_2OC(O)CH_2$-PH-$N(CH_3)_2$ | 677 | 55 |
| 102 | 1 | $CH_2OC(O)CH(CH_2)_5$ | 626 | 65 |
| 103 | 1 | $CH_2OC(O)$-PH-$CF_3$ | 688 | 85 |
| 104 | 1 | $CH_2OC(O)C(CH_3)_3$ | 600 | 108 |
| 105 | 1 | $CH_2OC(O)CH(CH_3)_2$ | 586 | 203 |
| 106* | 1 | $CH_2OC(O)CH(N*HC(O)OC(CH_3)_3)CH(CH_3)_2$ | 715 | 299 |
| 107 | 1 | $CH_2OC(O)CH(NHC(O)PH)CH_2PH$ | 767 | 706 |
| 108 | 1 | $CH_2OC(O)CH_3$ | 558 | 754 |
| 109 | 1 | $CH_2OH$ | 516 | 1337 |

B. Assays

EXAMPLE 14

Assay for Inhibition of Nitrendipine Binding

Female, New Zealand white rabbits (1–2 kg) are sacrificed by cervical dislocation, and the heart is immediately removed, cleaned and chopped into small pieces. The tissue is homogenized in 5× times volume of 0.05M Hepes buffer, pH 7.4. The homogenate is centrifuged at 4000 g for 10 minutes, and the supernatant is re-centrifuged at 42,000× g for 90 minutes. The resulting membrane pellet is resuspended (0.7 ml/g weight) in 0.05M Hepes, pH 7.4 and stored at 70° C. until used. Each tube of the binding assay contains $^3$H-nitrendipine (0.05–0.50 nM), buffer, membranes (0.10 ml), and test compound in a total volume of 1.0 ml. After 90 minutes at 4° C., the bound nitrendipine is separated from the unbound by filtration on Whatman GF/C filters. After rinsing, the filters are diried and counted in a liquid scintillation counter.

Non-specific binding of $^3$H-nitrendipine (that amount bound in the presence of excess unlabelled nitrendipine) is subtracted from the total bound to obtain specifically bcund radiolabeled nitrendipine. The amount of specifically bound nitreiidipine in the presence of a test compound is compared to that amount bound in the absence of a compound. A percent displacement (or inhibition) can then be calculated.

EXAMPLE 15

Test for Inhibition of Calcium-Dependent Smooth Muscle Contraction

The trachea and the aorta from dogs sacrificed by excess KCl injection are stored overnight at 4° C. in oxygenated Krebs-Henseleit buffer. Tracheal rings, one cartilage segment wide (5–10 mm), are cut starting from the bronchial end. Rings of aorta tissue of the same width are also prepared. After cutting the cartilage, the trachealis muscle tissue and the aorta tissue are suspended in oxyge(nated Krebs-Henseleit buffer at 37° C. in a 25 ml tissue bath. After a 60-minute equilibration period, the tissues are challenged with 10 μM carbachol. After 5 minutes, the tissues are rinsed and allowed to rest 50 minutes. The tissues are then challenged with 50 mM KCl and, after 30 minutes, the contractions are quantitated. The tissues are then rinsed and re-equilibrated for 50 minutes. Test compounds are then added for 10 minutes, and the tissue is rechallenged with 50 mM KCl. After 30 minutes, the contraction is recorded. A percent inhibition of smooth muscle contraction can then be calculated.

What is claimed is:

1. A compound of Formula I,

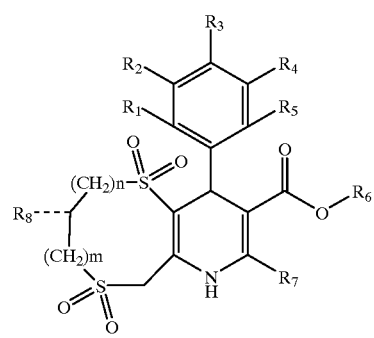

Formula I or a pharmaceutically acceptable salt thereof, wherein
(a) $R_1$, $R_2$, $R_3$, $R_4$ and $R_5$ are independently selected from the group consisting of H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl, and oxadiazole (formed by $R_1$ and $R_2$);
(b) $R_6$ is selected from the group consisting of H, $C_{1-5}$ straight or branched alkyl, aryl, 3-piperidyl, N-substituted 3-piperidyl, N-substituted 2-pyrrolidinyl methylene, and substituted alkyl, wherein
said N-substituted 3-piperidyl and said N-substituted 2-pyrrolidinyl methylene may be substituted with $C_{1-8}$ straight or branched chain alkyl or benzyl, and said substituted alkyl may be substituted with $C_{1-8}$ alkoxy, $C_{2-8}$ alkanoyloxy, phenylacetyloxy, benzoyloxy, hydroxy, halogen, p-tosyloxy, mesyloxy, amino, carboalkoxy or NR'R", wherein
(i) R' and R" are independently selected from the group consisting of H, $C_{1-8}$, straight or branched alkyl, $C_{3-7}$ cycloalkyl, phenyl, benzyl, and phenethyl, or (ii) R' and R" together form a heterocyclic ring selected from the group consisting of piperidino, pyrrolidino, morpholino, thiomorpholino, piperazino, 2-thieno, 3-thieno, and an N-substituted derivative of said heterocyclic rings, said N-substituted derivative being substituted with H, $C_{1-8}$ straight or branched alkyl, benzyl, benzhydryl, phenyl and/or substituted phenyl (substituted with $NO_2$, halogen, $C_{1-8}$ straight or branched chain alkyl, $C_{1-8}$ alkoxy and/or trinuoromethyl);
(c) $R_7$ is selected from the group consisting of H, amino, alkyl, aryl, trifluoromethyl, alkoxymethyl, 2-thieno and 3-thieno;
(d) $R_8$ is connected to the bis-sulfone ring via a single or double bond, as applicable, and is selected from the group consisting of H, alkylhydroxy, alkenyl, amino, phenyl, benzyl, $C_{1-8}$ straight or branched alkyl, trifluoromethyl, alkoxymethyl, $C_{3-7}$ cycloalkyl, substituted benzyl, formyl, acetyl, t-butyloxy carbonyl, propionyl, substituted alkyl and $R'''CH_2C=O$, wherein (i) said substituted benzyl is substituted with halogen, trifluoromethyl, $C_{1-8}$ straight and/or branched alkyl or $C_{1-8}$ alkoxy, (ii) said substituted alkyl is substituted with amino, dialkyl amino, $C_{1-8}$ alkoxy, hydroxy and/or halogen, and (iii) R''' is amino, dialkyl amino, $C_{1-8}$ alkoxy, hydroxy or halogen; and
(e) m, n, and their sum are each an integer from 0 to 4.

2. The compound of claim 1, wherein $R_6$ is —$(CH_2)_2N(CH_3)CH_2PH$.

3. The compound of claim 1, wherein $R_6$ is methyl.

4. The compound of claim 3, wherein $R_4$ is $CF_3$, $R_5$ is F, $R_7$ is methyl, $R_8$ is methylene, m is 0 and n is 1.

5. The compound of claim 3, wherein $R_4$ is $CF_3$, $R_5$ is F, $R_7$ is methyl, $R_8$ is alkylhydroxy, m is 0 and n is 1.

6. The compound of claim 1, wherein $R_7$ is methyl.

7. The compound of claim 6, wherein $R_6$ is —$(CH_2)_2N(CH_3)CH_2PH$.

8. The compound of claim 6, wherein $R_4$ is $CF_3$ and $R_5$ is F.

9. The compound of claim 6, wherein $R_5$ is Cl.

10. The compound of claim 6 wherein $R_1$ is F and $R_5$ is Cl.

11. The compound of claim 1 which is: 5H-1,4-Dithiepino [6,5-b]pyridine-8-carboxylic acid, 9-(2-chloro-6-fluorophenyl)-2,3,6,9-tetrahydro-7-methyl-2-[methyl(phenylmethyl)amino]ethyl ester 1,1,4,4-tetraoxide.

12. The compound of claim 1 which is: 5H-1,4-Dithiepino [6,5-b]pyridine-8-carboxylic acid, 2,3,6,9-tetrahydro-7-methyl-9-(3,4,5-trifluorophenyl)-2-[methyl(2-thienylmethyl)amino]ethyl ester 1,1,4,4-tetraoxide.

13. The compound of claim 1 which is: 5H-1,4-Dithiepino [6,5-b]pyridine-8-carboxylic acid, ]-[2-fluoro-6-(trifluoromethyl)phenyl]-2,3,6,9-tetrahydro-7-methyl-2-[methyl(phenylmethyl)amino]ethyl ester 1,1,4,4-tetraoxide.

14. The compound of claim 1 which is: 5H-1,4-Dithiepino [6,5-b]pyridine-8-carboxylic acid, 9-(2-chloro-6-fluorophenyl)-2,3,6,9-tetrahydro-7-methyl-2-[methyl (phenylmethyl)amino]ethyl ester 1,1,4,4-tetraoxide, (9R).

15. The compound of claim 1 which is: 5H-1,4-Dithiepino [6,5-b]pyridine-8-carboxylic acid, 9-(2-chloro-6-fluorophenyl)-2,3,6,9-tetrahydro-7-methyl-2-[methyl (phenylmethyl)amino]ethyl ester 1,1,4,4-tetraoxide, (9S).

16. The compound of claim 1 which is: 5H-1,4-Dithiepino [6,5-b]pyridine-8-carboxylic acid, 9-(2-chloro-6-hydroxyphenyl)-2,3,6,9-tetrahydro-7-methyl-2-[methyl (phenylmethyl)amino]ethyl ester 1,1,4,4-tetraoxide.

17. The compound of claim 1 which is: 5H-1,4-Dithiepino [6,5-b]pyridine-8-carboxylic acid, 9-(2-chlorophenyl)-2,3,6, 9-tetrahydro-7-methyl-2-[methyl(phenylmethyl)amino] ethyl ester 1,1,4,4-tetraoxide.

18. The compound of claim 1 which is: 5H-1,4-Dithiepino [6,5-b]pyridine-8-carboxylic acid, 9-[2-fluoro-3-(trifluoromethyl)phenyl]-2,3,6,9-tetrahydro-7-methyl-2-[methyl(phenylmethyl)amino]ethyl ester 1,1,4,4-tetraoxide.

19. The compound of claim 1 which is: 5H-1,4-Dithiepino [6,5-b]pyridine-8-carboxylic acid, 2,3,6,9-tetrahydro-7-methyl-9-(3-nitrophenyl)-2-[methyl(phenylmethyl)amino] ethyl ester 1,1,4,4-tetraoxide.

20. The compound of claim 1 which is: 5H-1,4-Dithiepino [6,5-b]pyridine-8-carboxylic acid, 2,3,6,9-tetrahydro-7-methyl-9-(3,4,5-trifluorophenyl)-2-[methyl(phenylmethyl) amino]ethyl ester 1,1,4,4-tetraoxide.

21. The compound of claim 1 which is: 5H-1,4-Dithiepino [6,5-b]pyridine-8-carboxylic acid, 9-(2-chloro-6-fluorophenyl)-2,3,6,9-tetrahydro-7-methyl-methyl ester 1,1, 4,4-tetraoxide.

22. The compound of claim 1 which is: 5H-1,4-Dithiepino [6,5-b]pyridine-8-carboxylic acid, 9-(2-chloro-5-nitrophenyl)-2,3,6,9-tetrahydro-7-methyl-methyl ester 1,1, 4,4-tetraoxide.

23. The compound of claim 1 which is: 5H-1,4-Dithiepino [6,5-b]pyridine-8-carboxylic acid, 2,3,6,9-tetrahydro-7-methyl-9-(pentafluorophenyl)-methyl ester 1,1,4,4-tetraoxide.

24. The compound of claim 1 which is: 5H-1,4-Dithiepino [6,5-b]pyridine-8-carboxylic acid, 9-(2,6-difluorophenyl)-2, 3,6,9-tetrahydro-7-methyl-methyl ester 1,1,4,4-tetraoxide.

25. The compound of claim 1 which is: 5H-1,4-Dithiepino [6,5-b]pyridine-8-carboxylic acid, 9-(2-chlorophenyl)-2,3,6, 9-tetrahydro-7-methyl-methyl ester 1,1,4,4-tetraoxide.

26. The compound of claim 1 which is: 5H-1,4-Dithiepino [6,5-b]pyridine-8-carboxylic acid, 9-(2-fluorophenyl)-2,3,6, 9-tetrahydro-7-methyl-methyl ester 1,1,4,4-tetraoxide.

27. The compound of claim 1 which is: 5H-1,4-Dithiepino [6,5-b]pyridine-8-carboxylic acid, 9-[2-fluoro-3-(trifluoromethyl)phenyl]-2,3,6,9-tetrahydro-7-methyl-methyl ester 1,1,4,4-tetraoxide.

28. The compound of claim 1 which is: 5H-1,4-Dithiepino [6,5-b]pyridine-8-carboxylic acid, 9-(2,3-difluorophenyl)-2, 3,6,9-tetrahydro-7-methyl-methyl ester 1,1,4,4-tetraoxide.

29. The compound of claim 1 which is: 5H-1,4-Dithiepino [6,5-b]pyridine-8-carboxylic acid, 2,3,6,9-tetrahydro-7-methyl-9-(2-nitrophenyl)-methyl ester 1,1,4,4-tetraoxide.

30. The compound of claim 1 which is: 5H-1,4-Dithiepino [6,5-b]pyridine-8-carboxylic acid, 9-[2-fluoro-3-(trifluoromethyl )phenyl]-2,3,6,9-tetrahydro-7-methyl-3-methylene-methyl ester 1,1,4,4-tetraoxide.

31. The compound of claim 1 which is: 5H-1,4-Dithiepino [6,5-b]pyridine-8-carboxylic acid, 9-[2-fluoro-3-(trifluoromethyl)phenyl]-2,3,6,9-tetrahydro-7-methyl-3-methylene-2-[methyl(phenylmethyl)amino]ethyl ester 1,1,4, 4-tetraoxide.

32. The compound of claim 1 which is: 5H-1,4-Dithiepino [6,5-b]pyridine-8-carboxylic acid, 9-[2-fluoro-3-(trifluoromethyl)phenyl]-2,3,6,9-tetrahydro-3-(hydroxymethyl)-7-methyl-methyl ester 1,1,4,4-tetraoxide.

33. The compound of claim 1 which is: 5H-1,4-Dithiepino [6,5-b]pyridine-8-carboxylic acid, 9-[2-fluoro-3-(trifluoromethyl)phenyl]-2,3,6,9-tetrahydro-3-

(hydroxymethyl)-7-methyl-2-[methyl(phenylmethyl)amino] ethyl ester 1,1,4,4-tetraoxide.

34. The compound of claim 1 which is: 5H-1,4-Dithiepino[6,5-b]pyridine-8-carboxylic acid, 2,3,6,9-tetrahydro-3-(hydroxymethyl)-7-methyl-9-(3-nitrophenyl)-2-[methyl(phenylmethyl)amino]ethyl ester 1,1,4,4-tetraoxide.

35. The compound of claim 1 which is: 2H,6H-1,5-Dithiocino[3,2-b]pyridine-9-carboxylic acid, 3,4,7,10-tetrahydro-8-methyl-10-(3-nitrophenyl)-2-[methyl(phenylmethyl)amino]ethyl ester 1,1,5,5-tetraoxide.

36. The compound of claim 1 which is: 2H,6H-1,5-Dithiocino[3,2-b]pyridine-9-carboxylic acid, 10-[2-fluoro-6-(trifluoromethyl)phenyl]-3,4,7,10-tetrahydro-8-methyl-2-[methyl(phenylmethyl)amino]ethyl ester 1,1,5,5-tetraoxide.

37. The compound of claim 1 which is: 2H,6H-1,5-Dithiocino[3,2-b]pyridine-9-carboxylic acid, 3,4,7,10-tetrahydro-8-methyl-10-(pentafluorophenyl)-2-[methyl(phenylmethyl)amino]ethyl ester 1,1,5,5-tetraoxide.

38. The compound of claim 1 which is: 2H,6H-1,5-Dithiocino[3,2-b]pyridine-9-carboxylic acid, 10-[2-fluoro-3-(trifluoromethyl)phenyl]-3,4,7,10-tetrahydro-8-methyl-2-[methyl(phenylmethyl)amino]ethyl ester 1,1,5,5-tetraoxide.

39. The compound of claim 1 which is: 2H,6H-1,5-Dithiocino[3,2-b]pyridine-9-carboxylic acid, 10-(2-chlorophenyl)-3,4,7,10-tetrahydro-8-methyl-2-[methyl(phenylmethyl)amino]ethyl ester 1,1,5,5-tetraoxide.

40. The compound of claim 1 which is: 2H,6H-1,5-Dithiocino[3,2-b]pyridine-9-carboxylic acid, 3,4,7,10-tetrahydro-8-methyl-10-(2-nitrophenyl)-2-[methyl(phenylmethyl)amino]ethyl ester 1,1,5,5-tetraoxide.

41. The compound of claim 1 which is: 4H-1,3-Dithiino[5,4-b]pyridine-7-carboxylic acid, 8-[2-fluoro-3-(trifluoromethyl)phenyl]-5,8-dihydro-6-methyl-2-[methyl(phenylmethyl)amino]ethyl ester 1,1,3,3-tetraoxide.

42. The compound of claim 1 which is: 4H-1,3-Dithiino[5,4-b]pyridine-7-carboxylic acid, 8-(2-chlorophenyl)-5,8-dihydro-6-methyl-2-[methyl(phenylmethyl)amino]ethyl ester 1,1,3,3-tetraoxide.

43. A compound of Formula (II),

II

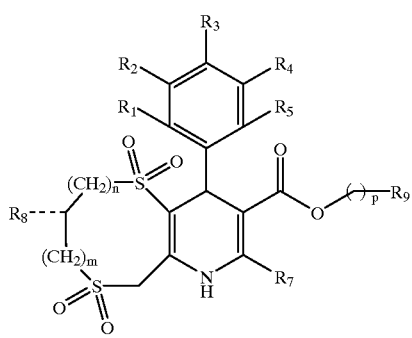

or a pharmaceutically acceptable salt thereof, wherein
(a) $R_1$, $R_2$, $R_3$, $R_4$ and $R_5$ are independently selected from the group consisting of H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl, and oxadiazole (formed by $R_1$ and $R_2$);
(b) $R_7$ is selected from the group consisting of H, amino, alkyl, aryl, trifluoromethyl, alkoxymethyl, 2-thieno and 3-thieno;
(c) $R_8$ is connected to the bis-sulfone ring via a single or double bond, as applicable, and is selected from the group consisting of H, alkylhydroxy, alkenyl, amino, phenyl, benzyl, $C_{1-8}$ straight or branched alkyl, trifluoromethyl, alkoxymethyl, $C_{3-7}$ cycloalkyl, substituted benzyl, formyl, acetyl, t-butyloxy carbonyl, propionyl, substituted alkyl and R'''CH$_2$C=O, wherein (i) said substituted benzyl is substituted with halogen, trifluoromethyl, $C_{1-8}$ straight and/or branched alkyl or $C_{1-8}$ alkoxy, (ii) said substituted alkyl is substituted with amino, dialkyl amino, $C_{1-8}$ alkoxy, hydroxy and/or halogen, and (iii) R''' is amino, dialkyl amino, $C_{1-8}$ alkoxy, hydroxy or halogen;
(d) $R_9$ is selected from -alkyl-OH, alkylamine, lactone, cyclic carbonate, alkyl-substituted cyclic carbonate, aryl-substituted cyclic carbonate, -aryl-C(O)OR', -alkyl-aryl-C(O)OR', -alkyl-OC(O)R', -alkyl-C(O)R', -alkyl-C(O)OR', -alkyl-N(R")C(O)R', and -alkyl-N(R") C(O)OR', wherein
R' and R" are independently selected from the group consisting of hydrogen, amino, alkyl, aryl, aryl-fused cycloalkyl, and heterocyclyl, the amino, alkyl, aryl, aryl-fused cycloalkyl, and heterocyclyl being optionally substituted with halogen, cyano, $NO_2$, lactone, amino, alkylamino, aryl-substituted alkylamino, amide, carbamate, carbamoyl, cyclic carbonate, alkyl, halogen-substituted alkyl, arylalkyl, alkoxy, heterocyclyl and/or aryl (the aryl being) optionally substituted with OH, halogen, cyano, $NO_2$, alkyl, amino, dimethylamino, alkoxy, alkylsulfonyl, $C_{1-4}$ carboalkoxy, alkylthio and/or trifluoromethyl);
(e) m, n, and their sum are each an integer from 0 to 4; and
(f) p is an integer from 0 to 4.

44. The compound of claim 43, wherein $R_9$ is -aryl-alkyl-OC(O)R'.

45. The compound of claim 43, wherein $R_9$ is -alkyl-N(R")C(O)R'.

46. The compound of claim 45 which is: 5H-[1,4]dithiepino[6,5-b]pyridine-8-carboxylic acid, 9-(2-chloro-6-fluorophenyl)-2,3,6,9-tetrahydro-7-methyl-, 2-[[(1,1-dimethylethoxy)carbonyl]amino]ethyl ester, 1,1,4,4-tetraoxide.

47. The compound of claim 43, wherein $R_9$ is -alkyl-OC(O)R'.

48. The compound of claim 47 which is: 5H-[1,4]dithiepino[6,5-b]pyridine-8-carboxylic acid, 9-(2-chloro-6-fluorophenyl)-2,3,6,9-tetrahydro-7-methyl-, 2-[[(1,2,3,4-tetrahydro-2-naphthalenyl)carbonyl]oxy]ethyl ester, 1,1,4,4-tetraoxide.

49. The compound of claim 47 which is: 5H-[1,4]dithiepino[6,5-b]pyridine-8-carboxylic acid, 9-(2-chloro-6-fluorophenyl)-2,3,6,9-tetrahydro-7-methyl-, 2-[(cycloheptylcarbonyl)oxy]ethyl ester, 1,1,4,4-tetraoxide.

50. The compound of claim 47 which is: 5H-[1,4]dithiepino[6,5-b]pyridine-8-carboxylic acid, 9-(2-chloro-6-fluorophenyl)-2,3,6,9-tetrahydro-7-methyl-, 2-[[4-(1-methylethoxy)benzoyl]oxy]ethyl ester, 1,1,4,4-tetraoxide.

51. The compound of claim 47 which is: 5H-[1,4]dithiepino[6,5-b]pyridine-8-carboxylic acid, 9-(2,3-dichlorophenyl)-2,3,6,9-tetrahydro-7-methyl-, 2-(2-methyl-1-oxopropoxy)ethyl ester, 1,1,4,4-tetraoxide.

52. The compound of claim 47 which is: 2H,6H-[1,5]dithiocino[3,2-b]pyridine-9-carloxylic acid, 10-(2-chloro-6-fluorophenyl)-3,4,7,10-tetrahydro-8-methyl-, 2-[[4-(1-methylethoxy)benzoyl]oxy]ethyl ester, 1,1,5,5-tetraoxide.

53. A pharmaceutical composition comprising the compound of claim 1 or 43 and a pharmaceutically acceptable carrier.

54. An apparatus for administering to a subject the pharmaceutical composition of claim 53, comprising a container and the pharmaceutical composition therein, whereby the container has a means for delivering to the subject a therapeutic and/or prophylactic dose of the pharmaceutical composition.

55. A process for preparing the compound of claim 1

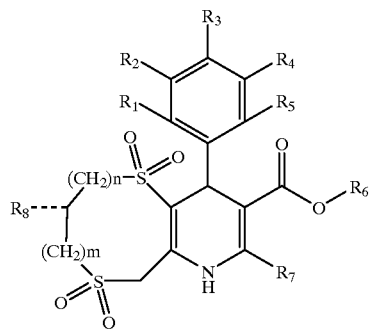

wherein m, n, and their sum are each an integer from 1 to 4, which process comprises the steps of (a) reacting the compound of Formula 1a with the compound of Formula 1b

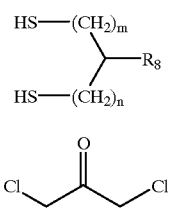

to form the compound of Formula 1c;

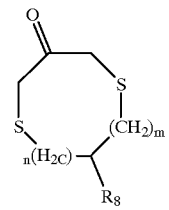

(b) reacting the compound of Formula 1c with m-chloroperoxybenzoic acid to form the compound of Formula 1d; and

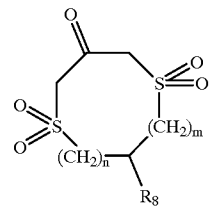

(c) reacting the compound of Formula 1d with the compounds of Formulae 1e and 1f

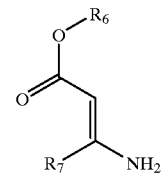

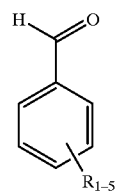

to form the compound of claim 1.

56. The process of claim 55, wherein $R_8$ of the compound of Formula I is a methylene group formed from a methylol group using a dehydrating agent.

57. A process of preparing the compound of claim 43,

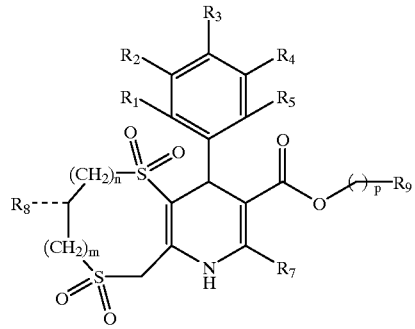

which process comprises the steps of (a) reacting the compound of Formula 3a' with formic acid to form the compound of Formula 3b'; and

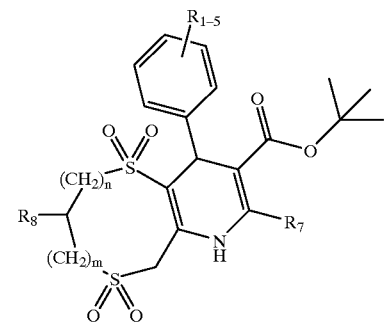

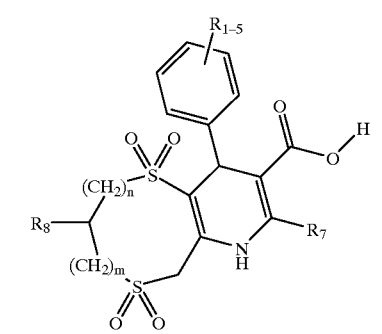

(b) reacting the compound of Formula 3b with $R_9Br$ or $R_9Cl$ to form the compound of claim 43.

58. The process of claim 57, wherein $R_7$ is methyl.

* * * * *